US010627471B2

(12) United States Patent
Medoff et al.

(10) Patent No.: US 10,627,471 B2
(45) Date of Patent: Apr. 21, 2020

(54) MONITORING METHODS AND SYSTEMS FOR PROCESSING BIOMASS

(71) Applicant: XYLECO, INC., Wakefield, MA (US)

(72) Inventors: Marshall Medoff, Brookline, MA (US); Thomas Craig Masterman, Rockport, MA (US); Dennis Michaud, Framingham, MA (US); Gerard Palace, Dracut, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

(21) Appl. No.: 16/400,648

(22) Filed: May 1, 2019

(65) Prior Publication Data

US 2019/0257908 A1    Aug. 22, 2019

Related U.S. Application Data

(63) Continuation of application No. 15/112,905, filed as application No. PCT/US2016/026495 on Apr. 7, 2016.

(60) Provisional application No. 62/143,850, filed on Apr. 7, 2015.

(51) Int. Cl.
   *G01R 33/60* (2006.01)
   *C13K 1/02* (2006.01)
   *C13K 13/00* (2006.01)

(52) U.S. Cl.
   CPC ............. *G01R 33/60* (2013.01); *C13K 1/02* (2013.01); *C13K 13/002* (2013.01); *C12P 2201/00* (2013.01)

(58) Field of Classification Search
   USPC ........................................................ 324/316
   See application file for complete search history.

(56) References Cited

U.S. PATENT DOCUMENTS

| | | | |
|---|---|---|---|
| 3,502,426 A | 3/1970 | Krassig et al. | |
| 3,844,890 A | 10/1974 | Horikoshi et al. | |
| 4,420,611 A | 12/1983 | Scheve | |
| 4,435,307 A | 3/1984 | Barbesgaard et al. | |
| 4,668,714 A | 5/1987 | Morita et al. | |
| 5,047,446 A * | 9/1991 | DeNicola, Jr. ............ | C08F 6/02 522/157 |
| 6,979,829 B2 * | 12/2005 | Calvert ................. | A61L 2/0035 250/472.1 |
| 7,473,435 B2 | 1/2009 | Koganov | |
| 7,900,857 B2 | 3/2011 | Medoff | |
| 7,931,784 B2 | 4/2011 | Medoff | |
| 7,932,065 B2 | 4/2011 | Medoff | |
| 7,971,809 B2 | 7/2011 | Medoff | |
| 8,074,910 B2 | 12/2011 | Medoff | |
| 8,083,906 B2 | 12/2011 | Medoff | |
| 8,142,620 B2 | 3/2012 | Medoff | |
| 8,236,535 B2 * | 8/2012 | Medoff ................... | C12P 19/02 435/162 |
| 8,318,453 B2 | 11/2012 | Medoff | |
| 8,377,668 B2 | 2/2013 | Medoff et al. | |
| 2010/0066366 A1 | 3/2010 | Cochrane et al. | |
| 2010/0093241 A1 | 4/2010 | Medoff | |
| 2010/0105119 A1 | 4/2010 | Medoff | |
| 2010/0124583 A1 | 5/2010 | Medoff | |
| 2010/0159569 A1 | 6/2010 | Medoff et al. | |
| 2012/0052536 A1 | 3/2012 | Medoff et al. | |
| 2012/0100577 A1 | 4/2012 | Medoff et al. | |
| 2012/0282379 A1 | 11/2012 | Medoff | |
| 2013/0052682 A1 | 2/2013 | Medoff et al. | |
| 2013/0052687 A1 | 2/2013 | Medoff et al. | |
| 2014/0011248 A1 | 1/2014 | Medoff et al. | |
| 2016/0355444 A1 * | 12/2016 | Olkowski ................ | C08H 6/00 |

FOREIGN PATENT DOCUMENTS

| | | |
|---|---|---|
| EP | 458162 A1 | 11/1991 |
| JP | S58-208301 A | 12/1983 |
| JP | S61-57878 A | 3/1986 |
| JP | S61-97585 A | 5/1986 |
| JP | 2006242870 A | 9/2006 |
| JP | 2007187641 A | 7/2007 |
| WO | 2006/102543 A2 | 9/2006 |
| WO | 2008/011598 A2 | 1/2008 |
| WO | 2008/073186 A2 | 6/2008 |
| WO | 2009/134816 A1 | 11/2009 |
| WO | 2010093829 A2 | 8/2010 |
| WO | 2010/135380 A1 | 11/2010 |
| WO | 2013096693 A1 | 6/2013 |
| WO | 2013096700 A1 | 6/2013 |
| WO | 2013101977 A1 | 7/2013 |
| WO | 2014059140 A1 | 4/2014 |
| WO | 2014139358 A1 | 9/2014 |
| WO | 2014159113 A1 | 10/2014 |
| WO | 2014205128 A1 | 12/2014 |

OTHER PUBLICATIONS

Ronnanyukha; et. al., "Electron paramagnetic resonance radiation dose assessment in fingernails of the victim exposed to high dose as result of an accident", Radiat Environ Biophys (2014) 53:pp. 755-762 (Year: 2014).*

Romanyukha et. al., "Electron paramagnetic resonance radiation assessment in fingernails of the victim exposed to high dose as result of an accident", Radiat Environ Biophys (2014) 53:755-762. (Year: 2014).*

Chu, William T., "Overview of Light-Ion Beam Therapy", Columbus-Ohio, ICRU-IAEA Meeting, Mar. 18-20, 2006.

Extended European Search Report from corresponding European Application No. 16777301.9 dated Feb. 15, 2019.

International Search Report and Written Opinion for application PCT/US2016/026495 dated Jul. 12, 2016.

Iwata, Y. et al., "Alternating-Phase-Focused IH-DTL for Heavy-Ion Medical Accelerators", Proceedings of EPAC 2006, Edinburgh, Scotland.

(Continued)

*Primary Examiner* — Phillip A Johnston
(74) *Attorney, Agent, or Firm* — Lando & Anastasi, LLP

(57) ABSTRACT

Systems and methods for monitoring and improving the treatment of biomass are described.

20 Claims, 21 Drawing Sheets

(56) References Cited

OTHER PUBLICATIONS

Leitner, C.M. et al., "Status of the Superconducting ECR Ion Source Venus", Proceedings of EPAC 2000, Vienna, Austria.
Partial Supplementary European Search Report from European Application No. 16777301.9 dated Nov. 14, 2018.
Prelec K. "Ions and Ion Accelerators for Cancer Treatement" FIZIKA B 6 (1997) 4, 177-206.
Romanyukha et al., "Electron paramagnetic resonance radiation dose assessment in fingernails of the victim exposed to high dose as result of an accident", Radiat Environ Biophys (2014), 53: 755-762.
Office Action from Japanese Application No. 2017-552052 dated Dec. 10, 2019.

* cited by examiner

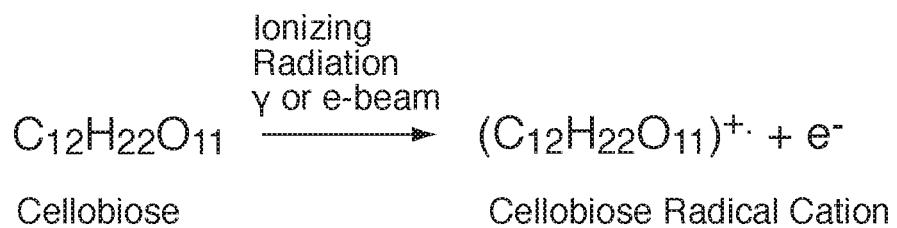
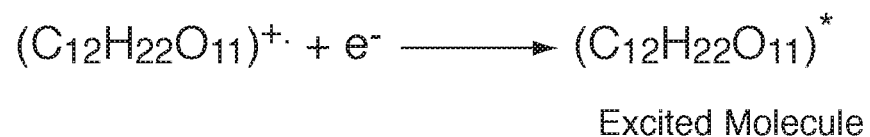
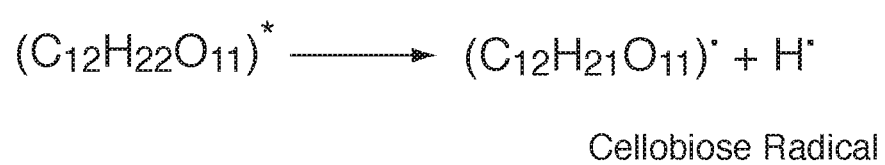
FIG. 3A

MONITORING METHODS AND SYSTEMS FOR PROCESSING BIOMASS

CROSS-REFERENCE TO RELATED APPLICATIONS

This application claims priority under 35 U.S.C. § 120 as a continuation of U.S. patent application Ser. No. 15/112,905, titled "MONITORING METHODS AND SYSTEMS FOR PROCESSING BIOMASS," filed Mar. 31, 2017, which is the U.S. National Phase Application under 35 U.S.C. § 371 of International (PCT) Patent Application Serial No. PCT/US2016/026495, titled "MONITORING METHODS AND SYSTEMS FOR PROCESSING BIOMASS," filed Apr. 7, 2016, which claims priority under 35 U.S.C. § 119(e) to U.S. Provisional Patent Application Ser. No. 62/143,850, titled "MONITORING METHODS AND SYSTEMS FOR PROCESSING BIOMASS," filed Apr. 7, 2015, the disclosures of which are hereby incorporated by reference in their entireties.

BACKGROUND

Many potential lignocellulosic feedstocks are available today, including agricultural residues, woody biomass, municipal waste, oilseeds/cakes and seaweed, to name a few. At present, these materials are often underutilized, being used, for example, as animal feed, biocompost materials, burned in a co-generation facility or even landfilled.

Lignocellulosic biomass includes crystalline cellulose fibrils embedded in a hemicellulose matrix, surrounded by lignin. This produces a compact matrix that is difficult to access by enzymes and other chemical, biochemical and/or biological processes. Cellulosic biomass materials (e.g., biomass material from which the lignin has been removed) are more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

SUMMARY

In general, methods, equipment and systems are disclosed herein for determining a dose of radiation a biomass material has received during treatment with ionizing radiation and for determining an optimum dose for maximum sugar yields from biomass.

At least one aspect of the invention is directed to a method, the method comprising irradiating a plurality of biomass portions, each portion being irradiated to a dose, and measuring an ESR response associated with each portion to produce a curve of response versus dosage.

According to one embodiment, the response measured is a total integrated response.

According to another embodiment, the curve is a polynomial. According to a further embodiment, the polynomial is a third degree polynomial. According to a further embodiment, the polynomial has a correlation coefficient with a value of at least 0.9. According to another embodiment, the correlation coefficient has a value of at least 0.92. According to another embodiment, the correlation coefficient has a value of at least 0.93. In one embodiment, the correlation coefficient has a value of at least 0.94. In another embodiment, the correlation coefficient has a value of at least 0.95. In another embodiment, the correlation coefficient has a value of at least 0.96. In another embodiment, the correlation coefficient has a value of at least 0.97. In another embodiment, the correlation coefficient has a value of at least 0.98. In another embodiment, the correlation coefficient has a value of at least 0.99.

According to another embodiment, the method further comprises irradiating a biomass sample and comparing to the curve of response versus dosage to determine a dose the biomass sample received. In one embodiment, the irradiating is performed with an electron beam.

According to one embodiment, the method further comprises storing at least one irradiated biomass portion for a predetermined time at a temperature below −50 degrees C. prior to the measuring. According to a further embodiment, the temperature is below −60 degrees C. In one embodiment, the temperature is below −70 degrees C. In another embodiment, the temperature is below −80 degrees C.

According to another embodiment, the measuring is performed less than 12 months after irradiation. In one embodiment, the measuring is performed less than 11 months after irradiation. According to one embodiment, the measuring is performed less than 10 months after irradiation. According to some embodiments, the measuring is performed less than 9 months after irradiation. In another embodiment, the measuring is performed less than 8 months after irradiation. In some embodiment, the measuring is performed less than 7 months after irradiation. According to one embodiment, the measuring is performed less than 6 months after irradiation. According to certain embodiments, the measuring is performed less than 5 months after irradiation. According to other embodiments, the measuring is performed less than 4 months after irradiation. According to some embodiments, the measuring is performed less than 3 months after irradiation. According to various embodiments, the measuring is performed less than 2 months after irradiation. According to at least one embodiment, the measuring is performed less than 1 month after irradiation. In one embodiment, the measuring is performed less than 4 weeks after irradiation. In another embodiment, the measuring is performed less than 3 weeks after irradiation. In some embodiments, the measuring is performed less than 2 weeks after irradiation. In one embodiment, the measuring is performed less than 1 week after irradiation.

According to another embodiment, the method further comprises heating at least one irradiated biomass portion for a predetermined time at a temperature above 50 degrees C. According to one embodiment, the temperature is above 60 degrees C. In one embodiment, the temperature is above 70 degrees C. In another embodiment, the temperature is above 80 degrees C. In some embodiments, the temperature is above 85 degrees C. In various embodiments, the temperature is above 90 degrees C. In at least one embodiment, the temperature is above 95 degrees C. In some embodiments, the temperature is above 100 degrees C. According to at least one embodiment, the temperature is above 105 degrees C.

According to one embodiment, each biomass portion is irradiated at a dose in a range of from about 0.1 Mrad to about 100 Mrad. In one embodiment, the dose is in a range of from about 1 Mrad to about 60 Mrad. In another embodiment, the dose is in a range of from about 1 Mrad to about 50 Mrad. In some embodiments, the dose is in a range of from about 2 Mrad to about 40 Mrad. According to another embodiment, each biomass portion is irradiated at a dose of between about 1 Mrad and a maximum dose, the maximum does associated with a dose where the response no longer increases with an increase in dose.

According to one embodiment, the biomass comprises a lignocellulosic material. According to some embodiments, the lignocellulosic material comprises an agricultural waste product, such as corn stover or corn cob.

According to another embodiment, the measuring occurs in an ESR tube. According to some embodiments, the ESR operates at a frequency in a range of from about 5 GHz to about 100 GHz. In some embodiments, the frequency is in a range of from about 5 GHz to about 50 GHz. In other embodiments, the frequency is in a range of from about 6 GHz to about 11 GHz.

According to at least one embodiment, the measuring comprises conducting a plurality of scans, the plurality of scans increasing the signal-to-noise ratio. In one embodiment, the number of scans is in a range of 2-256 scans. According to a further embodiment, the number of scans is in a range of 2-128 scans. According to yet a further embodiment, the number of scans is in a range of 4-64 scans.

At least another aspect of the invention is directed to method, the comprising irradiating a plurality of biomass portions, each portion being irradiated to a dose, measuring an ESR response associated with each portion to produce a curve of response versus dosage, and irradiating a bulk sample about a saturation dose determined from the curve. According to some embodiments, the bulk sample is irradiated within 50 percent of the saturation dose. In one embodiment, the bulk sample is irradiated within 25 percent of the saturation dose. In another embodiment, the bulk sample is irradiated within 10 percent of the saturation dose.

According to one embodiment, the method further comprises saccharifying the bulk sample.

At least another aspect of the invention is directed to a method, the method comprising saccharifying bulk biomass about a saturation dose, the saturation dose determined by irradiating a plurality of biomass portions, each portion being irradiated to a dose, and measuring an ESR response associated with each portion to produce a curve of response versus dosage.

According to another embodiment, the bulk biomass is irradiated within 50 percent of the saturation dose. According to one embodiment, the bulk biomass is irradiated within 25 percent of the saturation dose. According to a further embodiment, the bulk biomass is irradiated within 10 percent of the saturation dose.

Advantages of the systems and methods describe herein include the ability to quickly and accurately determine the dose a biomass material has received during processing. The methods and systems also provide the ability to monitor, control and optimize the process of irradiating biomass.

Other features and advantages of the invention will be apparent from the following detailed description, and from the claims.

BRIEF DESCRIPTION OF DRAWINGS

The foregoing will be apparent from the following more particular description of example embodiments of the invention, as illustrated in the accompanying drawings. The drawings are not necessarily to scale, emphasis instead being placed upon illustrating embodiments of the present invention.

FIG. 3A shows formation of a cellobiose radical cation, its neutral, excited molecular form and its radical form;

DETAILED DESCRIPTION

Using the equipment, methods and systems described herein, materials, such as starchy materials and/or cellulosic and lignocellulosic feedstock materials, for example that can be sourced from biomass (e.g., plant biomass, animal biomass, paper, and municipal waste biomass), can be turned into useful products and intermediates such as sugars and other products (e.g., fermentation products). Included are equipment, methods and systems to monitor, control and optimize the recalcitrance reduction in these feedstock materials, and to quickly and accurately determine a dose a biomass material has received during processing with ionizing radiation, such as electron beam radiation.

Figure 1:
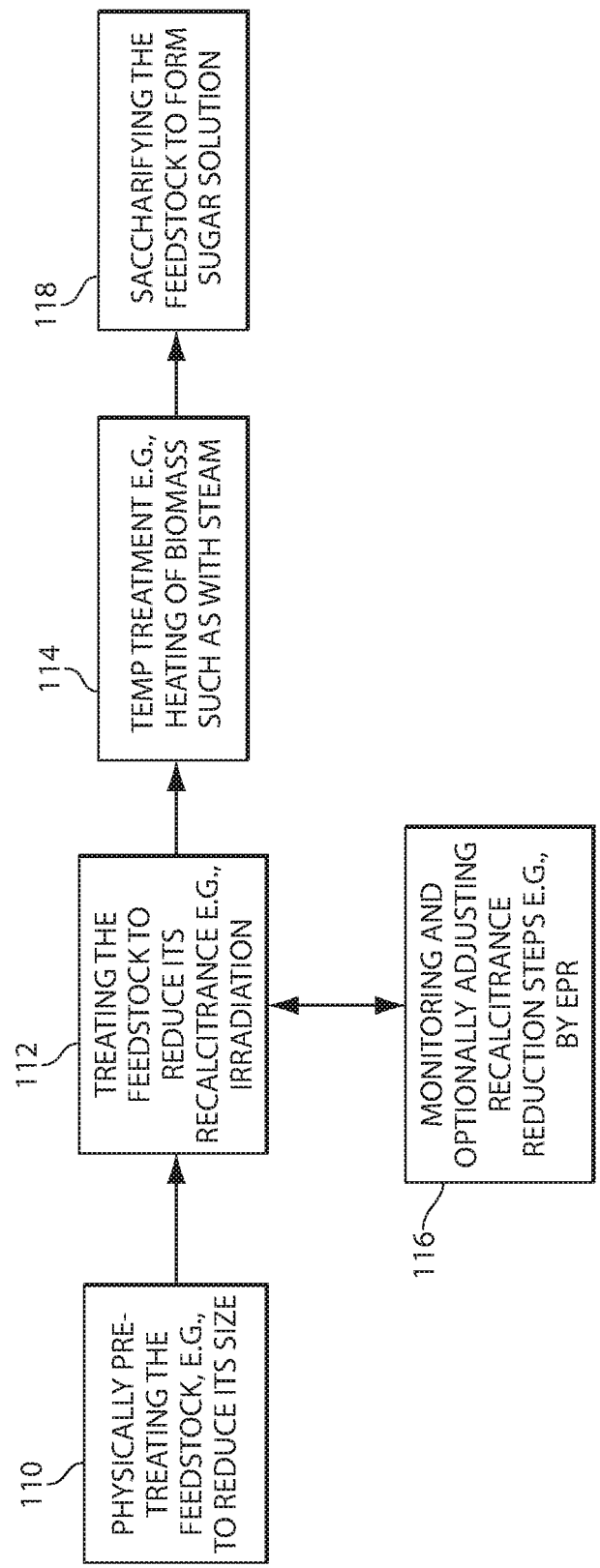
FIG. 1 is a flow diagram showing processes for manufacturing sugar solutions and products derived therefrom.

Referring to FIG. 1, processes for manufacturing sugar solutions and products derived therefrom include, for example, optionally mechanically treating a cellulosic and/or lignocellulosic feedstock 110. Mechanical treatments can, e.g., reduce the size of the biomass and/or reduce the recalcitrance of the biomass. Before and/or after this treatment, the feedstock can be treated with another physical, mechanical and/or chemical treatment, for example irradiation, to reduce, or further reduce its recalcitrance 112 or to change some other chemical or physical attribute of the material. After such treatments, the material can be heated 114, for example in air or in water or other liquid, to a target temperature such as above about 90 DEG. C. (e.g., between about 90 and about 200 DEG. C, between 92 and 130 DEG. C or between 94 Deg. C. and 115 Deg. C.), e.g., for a time sufficient, e.g., between 1 hour and 72 hours, between 3 hours and 48 hours or between 4 hours and 36 hours, to further reduce the recalcitrance of the material or to swell the material if the material is heated in water or another liquid. Steps 110, 112, and 114 can be monitored and/or adjusted, for example, based on the composition such as amount of lignin. For example, recalcitrance reduction and adjustments are discussed in PCT/US10/23957 filed Feb. 11, 2010, the entire disclosure of which is incorporated herein by reference. In addition, the recalcitrance reduction can be monitored by a detection method sensitive to a treatment-induced change in the material 116. For example, treatments such as electron beam irradiation of the material can produce radicals or charged radicals, such as radical cations thereupon and these can be detected, for example, by Electron Paramagnetic Resonance (EPR, also known as Electron Spin Resonance or ESR). After treatment steps (e.g., any one of more steps 110, 112 and 114 applied in any order and optionally repeated one or more times), a sugar solution or slurry can be formed by saccharifying the feedstock 118 by, for example, the addition of one or more enzymes and/or an acid. A product can be derived from the sugar solution, for example, by fermentation to an alcohol or an acid, such as lactic acid (in either stereoisomeric form). Further processing can include purifying the solution, for example by filtering and distillation.

Figure 2:
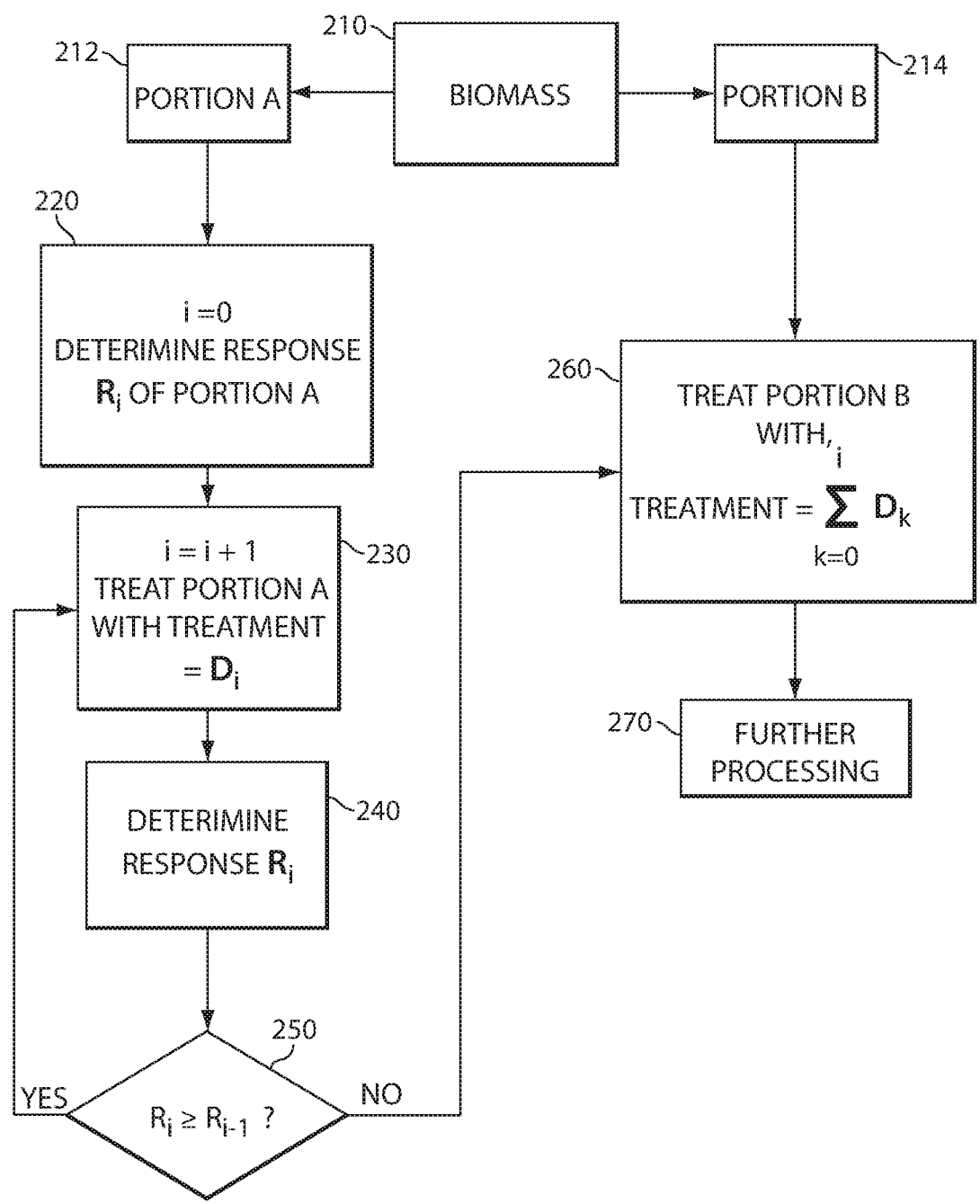
FIG. 2 is a flow diagram showing a method of monitoring and adjusting the recalcitrance reduction in a biomass.

FIG. 2 is a flow diagram showing a possible method of monitoring and adjusting the treatment level, e.g., recalcitrance reduction in a biomass, wherein the recalcitrance is reduced by a treatment and the treatment amount is measured by a detection method sensitive to a treatment-induced change in the biomass. Generally, the method can involve treating a biomass until the treatment cannot cause any more changes as indicated by measurement of a response, e.g., the treatment and corresponding response is saturated. In this method, biomass 210 is portioned into two portions, portion A 212 and portion B 214. In a first step 220, portion A is measured without any treatment, wherein the measurement response is designated $R_0$ where the "counter" i is an integer set in step 220 to be equal to zero (e.g., $R_i$ with i=0). In step 230, the counter i is incremented by 1 and the portion A of biomass is then treated with a measurable amount of treatment $D_i$ (e.g., $D_1$ with i=1 for the first treatment). In step 240 the "counter" i is incremented by 1 and the response $R_i$ (e.g., $R_1$ with i=1 for the first response measured after the first treatment) after the $D_i$ treatment is determined. Step 250 is a comparison step where response $R_{i+1}$ is compared to response $R_i$. If $R_i$ is greater than or equal to $R_{i-1}$, the process of treating 230, measuring 240, and comparing 250 are repeated. If $R_i$ is not greater than $R_{i-1}$, then the treatment can be set as indicated in step 260. The treatment that is set in step 260 is the treatment to apply to the portion B of the biomass and is a sum of the treatments as indicated by the formula:

$$\text{TREATMENT} = \sum_{k=0}^{i} D_k \qquad \text{Equation 1}$$

The treated material can subsequently be further processed in step 270. For example, the material can be treated with any additional recalcitrance reduction method such as by heating as described above. Alternatively or additionally the materials can be saccharified and/or converted to products as described herein (e.g., by fermentation to alcohols and/or other products).

When comparing values such as $R_{i-1}$ and $R_i$, it is understood that significant differences, for example as determined by the operator or comparison logic circuit, are acted upon. For example, if a response is noisy, the average of several measurements can be made, the number of measurements determined by the desired confidence in the number and the amount of noise in the signal. Statistical methods such as a T-test can be useful for determining these differences.

As an example, the treatment can be an irradiation with an electron beam where the dosage amount is controlled and is designated $D_i$. The response can be a response sensitive to radicals formed on and/or in the biomass such as an EPR response (e.g., such as a peak width, peak height or peak integration) and is designated $R_i$. At a dosage wherein no more irradiation will increase the amount of radicals formed, the total dose can be set as the sum of incremental dosages as in equation 1. In some instances, this total dose represents the optimal dose that the biomass should be treated for best sugar yields at lowest cost.

It should also be noted that the comparison step 250 can also be reversed depending on the nature of the treatment. That is, the comparison can be that if $R_{i-1}$ is greater than or equal to $R_i$, the process of treating and "counter" incrementing 230, measuring 240 and comparing 250 are repeated, and that if $R_{i+1}$ is not greater than $R_i$, then the treatment can be set as indicated in step 260. For example, the treatment could be a mechanical treatment such as milling a biomass, and the particle size is measured as the $R_i$ and $D_i$ is the time of milling. When no additional time of milling will further reduce the biomass material size $R_i$, (e.g., $R_i$ is greater or equal to $R_{i+1}$) the milling time can be set as the target time for step 260 (e.g., the sum of Di as indicated by equation 1). In an alternative example, the treatment can be a quenching reaction after an irradiation that produces radicals. As well be discussed further below, a quenching reaction can reduce the amount of radicals and if the response $R_i$ is sensitive to the amount of radicals, then this signal would decrease upon quenching.

Referring again to FIG. 2, portion A can be further partitioned into sub-portions, for example from 2 to 1000 portions (e.g., 2 to 100 portions, 2 to 50 portions). In such embodiments, each sub-portion is treated once and a response is determined for each sub-portion. For example, each sub-portion is sequentially treated with an increased amount of treatment. If each sub-portion is denoted $SP_i$, the treatment is $D_i$, and the Response is $R_i$ wherein $D_n > \ldots D_3 > D_2 > D_1$. For example Table 1 shows some possible values for counter, $SP_i$, $R_i$, and $D_i$.

TABLE 1

| Counter i | Portion $SP_i$ | Response $R_i$ | Treatment $T_i$ |
|---|---|---|---|
| 0 | $SP_0$ | $R_0$ | $T_0$ |
| 1 | $SP_1$ | $R_1$ | $T_1$ |
| 2 | $SP_2$ | $R_2$ | $T_2$ |
| 3 | $SP_3$ | $R_3$ | $T_3$ |
| n | $SP_n$ | $R_n$ | $T_n$ |

Treatments can include any treatment described herein, e.g., a recalcitrance reduction treatment. For example irradiation, sonication, heating, mechanical treatments, steam explosion, pyrolysis, chemical treatments and any combination of these. Many of these methods are described in detail below.

The response can be dependent on the treatment and material. For example, the response that is measured can be a pH, a temperature change, the moisture content, hydrophobicity, hydrophilicity, a conductivity, a porosity, a density, a UV-Vis absorbance, an NMR signal, an EPR signal, an FUR signal, a thermal conductivity, a compressibility, or a combination of these. For example the signal can be due to a measurement instrument such as from chromatography (e.g., liquid, gas chromatography), a spectrophotometer, an NMR spectrometer, an EPR spectrometer, an ion selective meter, a pH meter, a viscometer, a power meter, a conductivity meter, a potentiometer, a voltmeter or any combination of these methods.

The treatment amount designated $D_i$ herein, depends on the kind of treatment. For example, for ionizing radiation, the treatment can be a dose, the energy of electrons and/or the penetration depth of the radiation. Alternatively, for example, for a wet milling recalcitrance reduction treatment, the treatment amount might be monitored by the output in kWh of a motor driving the wet milling apparatus. In case of a chemical treatment, such as the addition of peroxide and a Fenton reagent, the amount of peroxide and Fenton reagent, the ratio of these, and the ratio of these to the amount of material treated can each be the designated $D_i$. In a quenching reaction such as quenching with a gas such as oxygen, the concentration of the gas, the flow rate of the gas through the material, and the pressure of the gas applied to the material can each be the designated $D_i$.

Electron Paramagnetic Resonance (EPR) is one method for measuring radicals or charged radicals, e.g, radical cations, in biomass. More specifically, the EPR experiment can be used to measure the amount, type, and kinetics (e.g., formation rates, quenching rates, transfer rates) of radicals on biomass, e.g., cellulosic or lignocellulosic materials. EPR spectroscopy is similar to other techniques that depend on electromagnetic radiation and is a non-destructive method. An isolated electron has an intrinsic angular momentum called spin ($\overline{S}$). Since electrons are charged, the angular motion generates a magnetic field and acts like a magnetic dipole with a magnetic moment ($\overline{\mu}$). Placing unpaired electrons in a magnetic field gives rise to an energy split between the spin up and spin down state as the magnetic dipoles align with the magnetic field. This is known as the Zeeman Effect and it is this energy difference that is interrogated by EPR.

The energy difference for a free electron is determined by Equation 2 as shown below.

$$\Delta E = g_e \beta B_o \quad \text{Equation 2}$$

where $g_e$ is the spectroscopic g-factor of a free electron which is 2.0023 (~2), $\beta$ is the Bohr magneton and $B_o$ is the magnetic field. Therefore, for a free electron, the only variable is the magnetic field.

Due to spin-orbit coupling the energy difference is modified and the energy is represented by Equation 3 below.

$$\Delta E = g \beta B_o = h\nu \quad \text{Equation 3}$$

In Equation 3, g contains the contribution from the spin-orbit coupling and contains chemical information on the electronic structure of the molecule. The relationship to Plank's constant, h, and frequency $\nu$ is also shown in Equation 3. The value of g strongly depends on the size of the nucleus containing the unpaired electron. Therefore, organic free radicals, typically with only H, O, and N atoms, will have a small contribution from spin-orbit coupling, producing g factors close to $g_e$ while the g factors of larger elements such as metals, may have significantly different values from $g_e$.

Since $\beta$ is constant and the magnitude of $B_o$ can be measured, the values of g can be calculated by determining $\Delta E$. This can be accomplished by irradiating the sample with microwaves at a set frequency and sweeping the magnetic field. Typically, microwave energy is the X-band from a klystron as the set frequency, for example with energies around 9.75 GHz. Absorption of energies will occur when the conditions in Equation 3 is satisfied. This is one form of the EPR experiment.

The interaction of the unpaired electron with the surroundings can further modulate the peak positions. Interactions with a nuclear magnetic moment is termed "nuclear hyperfine interaction." This interaction is sometimes termed a "hyperfine interaction" if it results from the nucleus where the unpaired electron originates and "superhyperfine" if it is from a neighboring nucleus. Another type of interaction is the interaction between two unpaired electrons on different atoms normally within a molecule, known as spin-spin interaction. These interactions provide a wealth of information as to the structure of the molecule being probed, such as the identity and number of atoms which make up a molecule or complex, as well as their distances from the unpaired electron. For example, proximity to a proton can cause a splitting of a band due to the proton nuclear spin. Additional protons can cause further splitting of the band. In complex molecules, the hyperfine and spin-spin interactions can serve as a fingerprint for a particular structure.

As discussed above, the positions of adsorption bands can determine or be a fingerprint for a particular molecule or functionality. In addition, the magnitude of the EPR signal can be used to measure the concentration of an EPR active species. The integrated intensity of an EPR signal can be proportional to the concentration of radicals present in the sample.

Free radicals formed on biomass can reside on many different sites due to the large and complex structure of biomass and can at times move from site to site. The different environments of these radicals can lead to overlapping signals that can be dynamic making the extraction of useful signal information a challenge. The methods herein can be useful to extract useful signal information. The following describes some of the kinds of biomass that can be utilized in the methods described herein as well as radicals formed therein, their detection and how the radicals might be formed.

Biomass is a large and diverse group of materials. For example, biomass can include many different materials such as starchy materials, cellulosic or lignocellulosic materials. Non-limiting examples include paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), algae, seaweed, manure, sewage, and mixtures of any of these.

Furthermore, as a subset of biomass, lignocellulosic materials comprise different combinations of cellulose, hemicellulose and lignin. Cellulose is a polysaccharide of glucose in a linear arrangement. The linear arrangement forms a stiff structure without significant coiling. Due to this structure and the disposition of hydroxyl groups that can hydrogen bond, cellulose contains crystalline and non-crystalline portions. The crystalline portions can also be of different types, noted as I(alpha) and I(beta) for example, depending on the location of hydrogen bonds between strands. The polymer lengths themselves can vary lending more variety to the form of the cellulose. Hemicellulose is also a polysaccharide and is any of several heteropolymers, such as xylan, glucuronoxylan, arabinoxylans, and xyloglucan. The primary sugar monomer present is xylose, although other monomers such as mannose, galactose, rhamnose, arabinose and glucose are present. Typically hemicellulose forms branched structures with lower molecular weights than cellulose. Hemicellulose is therefore an amorphous material that is, for example, generally susceptible to enzymatic hydrolysis. Lignin is a complex high molecular weight heteropolymer generally. Although all lignins show variation in their composition, they have been described as an amorphous dendritic network polymer of phenyl propene units. The amount of cellulose, hemicellulose and lignin in a specific biomaterial depends on the source of the biomaterial. For example wood derived biomaterial can be about 38-49% cellulose, 7-26% hemicellulose and 23-34% lignin depending on the type. Grasses typically are 33-38% cellulose, 24-32% hemicellulose and 17-22% lignin.

Other components of biomass can include proteinaceous material. The principal structural elements are polypeptide chains, although they may be combined with fats as lipoproteins and with polysaccharides as glycoproteins. Proteins have complex structures based on their amino acid composition, three dimensional structures (helices, beta sheets), and the way subunits are linked together. Molecular weights vary from thousands to millions Dalton. The molecules may consist of one single chain or two or more chains joined by disulfide bonds. Globular proteins consist of chains tightly intertwined to form a nearly spherical shape. In some more complex proteins these spherical units may themselves be joined together by non-covalent forces into larger structures of fairly precise form.

Proteins can be found in several agro-materials, plants and animals. Proteins play an important role in the diets of animals and humans and other organisms such as microorganisms. Traditionally, for food consumption cereals (e.g. wheat, barley and sorghum), legumes (green peas, lentils, beans and chick peas) and nuts are being grown. Animal sources include meat, hides and bone. A number of proteins have been produced commercially for a long time. These proteins, such as soy proteins, pea proteins, maize proteins, dairy proteins, and wheat proteins, are being used both in food and non-food area. Newer protein sources include the cellulosic and lignocellulosic materials previously discussed. Some high protein sources include bioproducts of processing of biomass materials such as from press cakes from sunflower or rapeseed processing or distillers grains. Distillers dry grains are described in U.S. application Ser. No. 13/440,107 filed on Apr. 5, 2012 the entire disclosure of which is incorporated herein by reference. Some examples of proteins that can be found in proteinaceous materials include albumins, globulins (e.g., legumin, vacilin, glycinins and conglycinins), gluten (e.g., gliadins and glutenins), casein, whey, collagen, gelatin, zein, glutelin, keratin, lectines, patatin, hemoglobin, cruciferin and napin. In addition to the above mentioned sources proteins in biomass can be sources from microalgae, insects, microorganisms, animal bones, animal hides, grass, Lucerne, alfalfa, plant leaves, spinach leaves, beet leaves and jathropa leaves.

Free radicals can be produced on biomass materials from treatment, e.g., for recalcitrance reduction. For example, mechanical methods such as milling, cutting, extruding, pressing, shearing, and grinding can produce radicals due to bond breaking (e.g., in polymers such as saccharides, lignin and proteins). Treatment with chemical agents such as peroxide and metals can produce radicals on biomass, for example as described in U.S. patent application Ser. No. 12/639,289 filed on Dec. 16, 2009 the entire disclosure of which is incorporated herein by reference. As another example, pyrolysis can produce radicals on biomass components. During pyrolysis, gasification and combustion of biomass polycyclic aromatic hydrocarbons (PAHs) are produced. These are generally considered to be environmental pollutants and soot precursors, the production of which should be controlled and preferably minimized. PAHs are believed to be formed by pyrosynthesis in which radicals undergo a series of bimolecular reactions with alkenes, alkynes, and aromatics to form larger ring structures. Sonication can also produce radicals on biomass components. The introduction of a strong acoustic field to an aqueous solution containing biomass results in the generation of cavitation microbubbles. The growth and collapse of these microbubbles focuses and transfers energy from the macroscale (acoustic wave) to the micro-scale (vapor inside the bubbles) producing extremely high localized pressures and temperatures. This unique energy focusing process generates highly reactive free radicals such as hydroxyl radicals, hydroperoxide radicals, hydride, and dihydrogen oxide radicals. These radical species can then react with biomass components, for example, by hydrogen extraction producing radicals on the biomass. In some preferred embodiments, methods of recalcitrance include treatment with ionizing radiation which also produces free radicals on biomass. For example, preferred methods include electron beam irradiation as described herein.

Figure 3B:
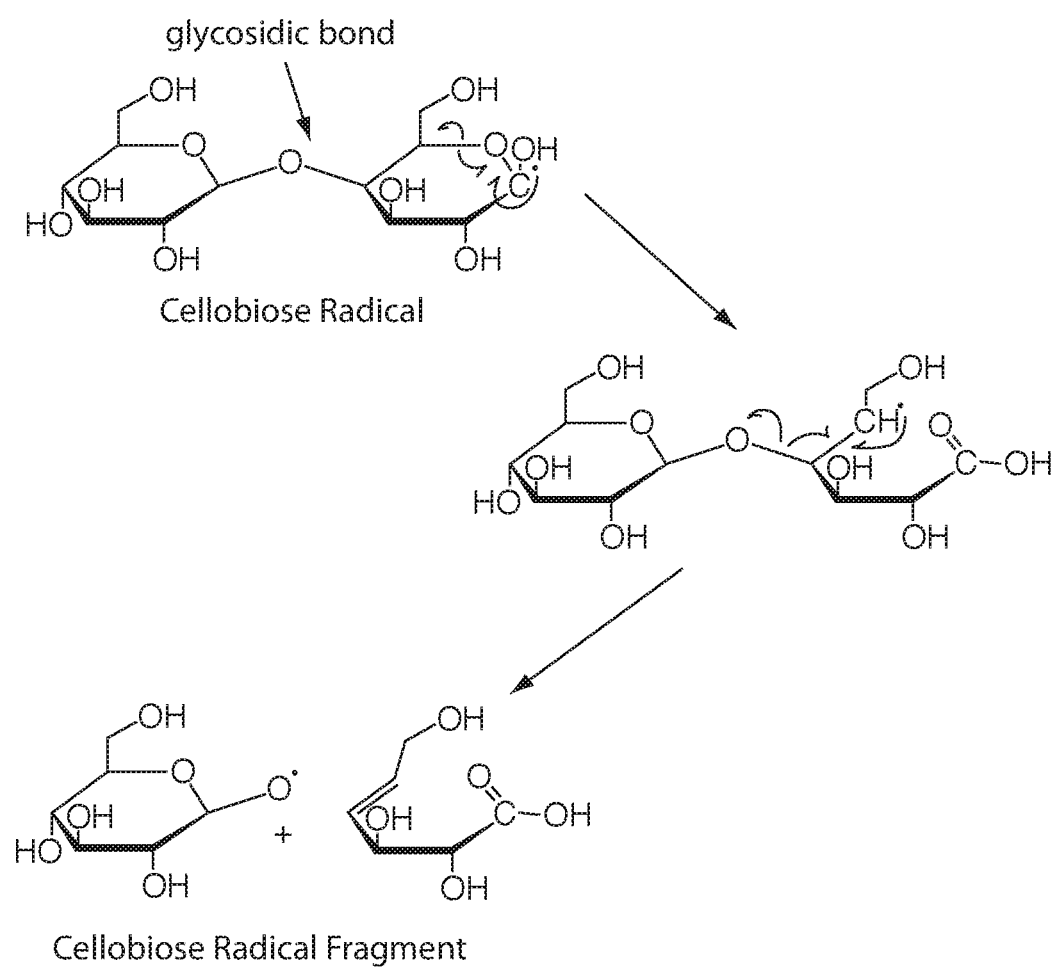
FIG. 3B shows possible chain scission reactions occurring on cellobiose.

Irradiation of polysaccharides in solid state can induce radical formation in molecular chains as a result of the direct action of radiation. Although radicals and radical cations (and other similar species) are very reactive, in the solid state, especially in crystalline domains, such species can have a long lifetime. FIG. 3A shows that when cellobiose is irradiated with ionizing radiation, such as gamma rays or accelerated electrons, a radical cation of cellobiose is generated, along with secondary electrons. The radical cation of cellobiose combines with an electron to produce a neutral, non-radical species that is energetically in an excited state. This excited molecule falls apart to form a cellobiose radical and a hydrogen atom. FIG. 3B is a simplification highlighting possible chain scission reaction on polysaccharides with the model compound cellobiose, a dimer of glucose and the smallest unit having a glycosidic bond. Scission of the glycosidic bond, as shown in FIG. 3B, is considered to be a dominant process that can lead to a decrease in the molecular weight when cellulosic or lignocellulosic materials are irradiated. This reduction in molecular weight can contribute to recalcitrance reduction in a cellulosic or lignocellulosic material or enhanced solubility in a starchy material. Hydrolysis reactions can occur due to moisture that is present and, for at least for this reason, the radiation products can be strongly influenced by the moisture present. In addition to hydrolysis, water can affect the reaction pathways and products due to contribution of water radiolysis, where the yields of radicals are significantly higher than in dry polysaccharide, and can contribute in indirect radiation effects (e.g., reactions of the polysaccharides with hydroxyl radicals). Water can also affect the dry matrix structure and polymer chain mobility. In solution, the radiation effect on polysaccharides will be predominantly secondary since the primary event will be radiolysis of water and the induced radicals can then react with cellulosic materials. This can be a less efficient method for reducing the molecular weight. For these reasons, among others, the control of water content in cellulosic material can be important to control molecular weight reduction/recalcitrance reduction.

As noted, FIGS. 3A and 3B depicts a simplification of polysaccharide irradiation since this figure depicts the irradiation of a monomeric species. Without being bound to any specific theory, it is noted that often the first event observed during the irradiation of polysaccharides is the breakdown of the ordered system of intermolecular as well as intra molecular hydrogen bonds. A consequence of this is that the rigidity of chains, which is strongly influenced by intramolecular hydrogen bonding, and the degree of crystallinity of the material (e.g., cellulose, lignocellulose) decreases. In addition, if a partially crystalline polysaccharide, such as cellulose which can have crystalline domains, is irradiated in the solid state (or any other state where the partially crystalline structure is retained), some of the initially formed radicals may become trapped in crystalline regions and remain there for a long time (hours to months or even longer) after irradiation. These "frozen" radicals may slowly migrate to the boundaries of crystalline regions, where they can undergo reactions of similar mechanisms as those occurring directly under irradiation. Besides the very slow migration, other processes (changes in crystalline structure due to external conditions, migration of traces of water) may make these dormant radicals available for reaction. Post-irradiation effects may occur for samples irradiated and stored both in the presence and absence of oxygen.

Too much irradiation can cause decomposition of the carbohydrates. In some embodiments it has been found that irradiation too far above the radical saturation point can be detrimental or may provide no additional benefit in terms of sugar yields. Part of this can be due to heat degradation as discussed herein. Another possibility is that too much radiation induces degradation of the polysaccharides, where glucose is fragmented eventually to small volatile molecules such as carbon dioxide, water, formaldehyde and/or to denser products such as aromatic compounds and char. In preferred embodiments the amount of radicals produced in a biomass, such as through irradiation, is controlled. In some embodiments irradiation above 100 Mrad and more preferably above about 50 Mrad is avoided.

In some embodiments, for example, for optimum sugar yields at the least cost, the biomass is irradiated within 50 percent (below or above) of the saturation point, e.g., within 40, 30, 25, 20, 10, 5 or substantially at the saturation point.

Irradiation can also give rise to lignin based radicals. Due to the high amounts of aromatic functional groups (e.g., phenol groups, aryl ethers, alkyl aromatic compounds) lignin can form stable radicals and has been considered to be an anti-oxidant/radical scavengers. Conversely, lignin model compounds are known to undergo oxidative decomposition if irradiated by UV light and decompose through radical propagated mechanisms. Without being bound to a specific mechanism, it is believed that irradiation of biomass containing lignin can degrade lignin by radical mediated mechanism, either through direct reaction or through hydroxyl radical mediated reactions. This degradation can contribute to recalcitrance reduction, for example, in biomass containing lignocellulosic material. Preferably the amount of radicals produced in a biomass containing lignin is controlled so as to provide an adequate degree of recalcitrance reduction. For example, the production of radicals can be managed and controlled by electron beam irradiation between about 10 Mrad and 200 Mrad.

Irradiation of biomolecules such as proteins, amino acids, fats, vitamins and DNA can be destructive to these molecules. In fact irradiations below 5 Mrad (e.g., below 4 Mrad, below 3 Mrad, below 2 Mrad, below 1 Mrad, below 0.1 Mrad) can be used for sterilizing organic materials by killing contaminating organisms (e.g., bacteria, yeasts or insects) or reducing their ability to reproduce. Sterilization can be primarily due to the destruction of DNA, but effects on other biomolecules are also evident. For example, irradiation of proteins can lower the biological value of proteins as a nutrient, for example irradiation above about 10 Mrad (e.g., above 20 Mrad, above about 50 Mrad) will significantly impact a proteins biological value and net utilization by organisms. Vitamins (e.g., Vitamin C, Vitamin E and Thiamine) can be particular susceptible to destruction by irradiation. Poly unsaturated fatty acids are susceptible to irradiation particularly through attack of the unsaturated bonds through secondary ionization processes, such as attach by hydroxyl radicals (e.g., generated from irradiated water). Therefore, the irradiation of biomass containing these biomolecules can reduce the biomass nutritional value. Since these nutrients can be useful to organisms that may be utilized in downstream processing of the biomass (e.g., for production of enzymes, alcohols, acids or other products through fermentation), it is preferable to control the production of radicals (discussed below) through irradiation. For example, the irradiation dosage should be sufficient to reduce the recalcitrance of the biomass but also targeted to minimize the destruction of the nutrient value of the biomass (e.g., between about 10 Mrad and about 100 Mrad, between about 10 and 50 Mrad, between about 20 and 40 Mrad). Preferably the amount of irradiation is minimized to avoid any nutrient destruction. Alternatively or additionally, nutrients can be added to the biomass after irradiation, for example as described in U.S. patent application Ser. No. 13/184,138 filed Jul. 15, 2011, the entire disclosure of which is incorporated herein by reference.

Figure 4:
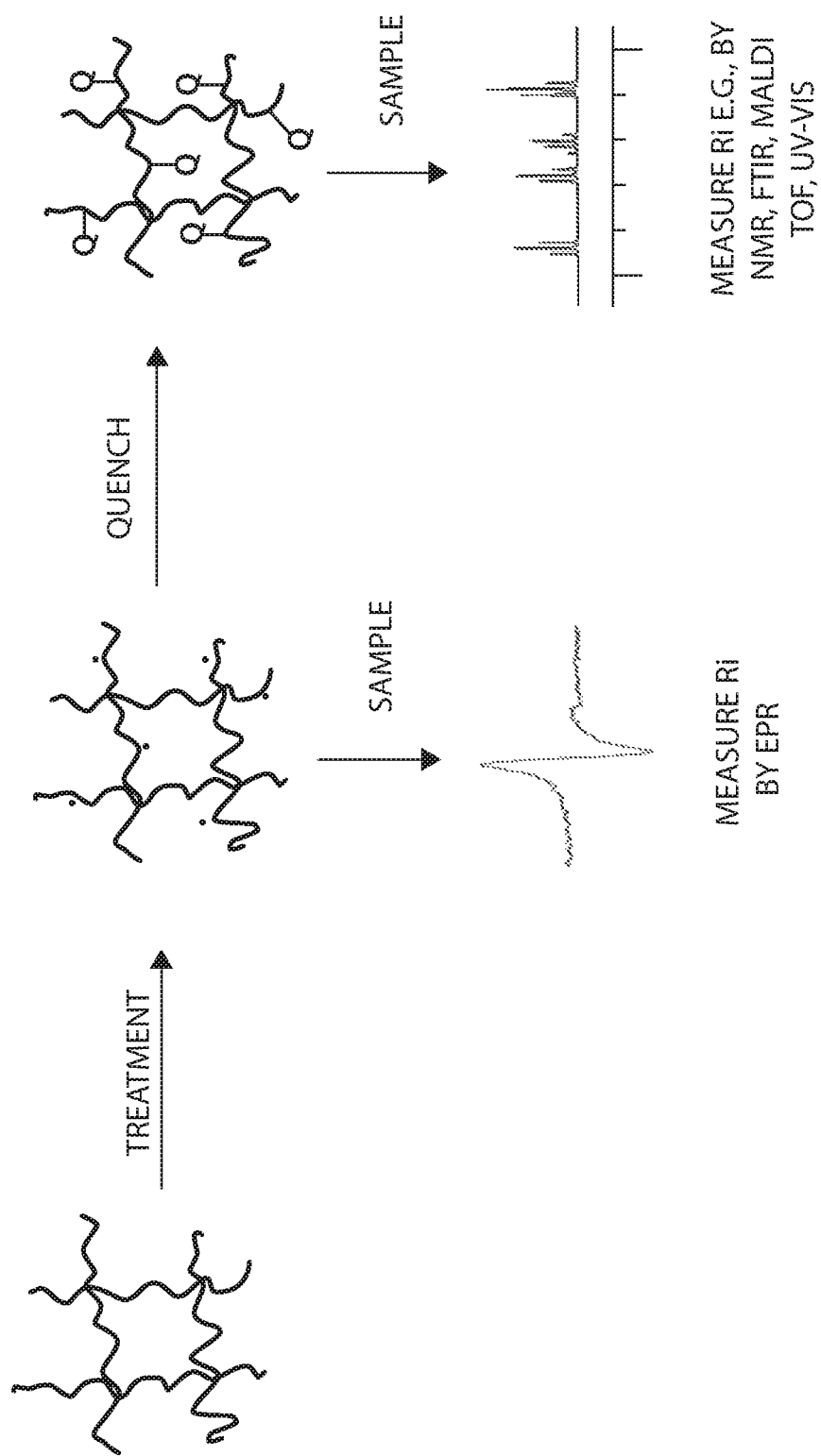
FIG. 4 is a schematic representation of the formation and quenching of radicals and the detection of the same.

Radicals (e.g., formed on biomass) can be quenched by various mechanisms. For example, the biomass can be contacted with a fluid or gas containing molecules or atoms that will react with the radicals. For example, if ionized biomass containing radicals remains in the atmosphere, oxidation can occur through the reaction of atmospheric oxygen and pendent carboxylic acid groups can form on the biomass (e.g., on saccharide units). In some instances with some materials, such oxidation is desired because it can aid in the further breakdown in molecular weight of the carbohydrate-containing biomass, and the oxidation groups, such as carboxylic acid groups, can be helpful for solubility and microorganism utilization. Additionally, radical quenching can produce functional groups other than carboxylic acid if biomass containing radicals are quenched with gases or liquids other than or in addition to oxygen, e.g., forming functional groups such as enol groups, aldehyde groups, ketone groups, nitrile groups, nitro groups, or nitroso groups on the biomass. The formation of functionalized biomass is described in U.S. Pat. No. 8,377,668 filed May 18, 2010 and issued Feb. 10, 2013 and in PCT Application PCT/US09/42000 filed Apr. 28, 2009, the entire disclosures of which are incorporated herein by reference. The formation of such groups can be utilized in the methods described herein to produce a response signal $R_i$, for example by UV-vis spectroscopy, Nuclear Magnetic Resonance spectroscopy (e.g. $^1$H NMR, $^{13}$C NMR or $^{14}$N or $^{15}$N NMR), Fourier Transform Infrared Spectroscopy (FTIR) spectroscopy and/or Mass Spectroscopy (e.g. MALDI TOF or ESI). FIG. 4 pictorially shows how macromolecules (e.g., polysaccharides) can be treated to produce radicals thereupon. The treated biomass can be sampled and a response Ri can be measured by EPR. Optionally or additionally, the treated biomass can be quenched with a fluid (e.g., a liquid or gas) producing functional groups "Q" pendent on the biomass macromolecules. The functionalized biomass can then be probed by an appropriate method to produce a response $R_i$, such as by utilizing a spectroscopic method (e.g., NMR, FTIR, MALDI TOF, ESI or UV-Vis).

Functional groups can be formed on the materials disclosed herein including a plurality of saccharide units arranged in a molecular chain, wherein from about 1 out of every 2 to about 1 out of every 250 saccharide units includes a functional group. In another aspect, materials include a plurality of such molecular chains. For example, about 1 out of every 8, 1 out of every 10, 1 out of every 50, or 1 out of every 100 saccharide units of each chain can include a functional group. In some embodiments, the saccharide units can include 5 or 6 carbon saccharide units. Each chain can have between about 10 and about 200 saccharide units, e.g., between about 10 and about 100 or between about 10 and about 50. For example, each chain can include hemicellulose or cellulose.

Biomass based radicals can also "live" for some time after irradiation, e.g., longer than 1 day, 5 days, 30 days, 3 months, 6 months or even longer than 1 year. In particular, some radicals can have a longer lifetime than others, and therefore the material properties of the biomass can continue to change over time as some radicals are slowly quenched. In particular, in the absence of an efficient quenching agent contacting the biomass, self-quenching, such as by coupling of two radicals or by beta hydrogen elimination and formation of unsaturated bonds, proceeds slowly. In addition, the transfer of radicals from more reactive sites such as a primary C, to a secondary carbon, to a tertiary carbon of to an aromatic system can also occur. In addition, carbon centers with electron withdrawing groups or aromatic systems where the electron can be stabilized, can also form a natural energy sink of the system. The transfer of electrons and self quenching reactions can be facilitated by heating the sample with free radicals since this can increase the mobility of the radicals (e.g., a polysaccharide). Conversely, cooling the sample can slow down or even stop these processes.

In some preferred embodiments the material (e.g., biomass) that has electrons can be cooled to stabilize or "freeze" any radicals thereupon. For example the biomass can be cooled to below room temperature such as below about 25 deg C., below about 0 deg C., below about −10 deg C., below about −20 deg C., below about −30 deg C., below about −40 deg C., below about −50 deg C., below about −60 deg C., below about −70 deg C.).

In some preferred embodiments a sample that has radicals thereupon can be heated to about room temperature (e.g., about 25 deg C.), above about 40 deg C., above about 60 deg C., above about 80 deg C., above about 100 deg C.). Conversely, the temperatures cannot be so high as to destroy the material. For example the material (e.g., biomass) can be heated to a temperature below about 200 deg C. (e.g., below about 180 deg C., below about 160 deg C., below about 140 deg C., below about 120 deg C.). This heat treatment can help in quenching some of the radicals (e.g., by hydrogen abstraction or coupling reactions) and thermally stabilizing others (e.g., providing enough activation energy for the radicals to move to another site)

In some embodiments the materials are both heated and cooled in any order and repeatedly. For example, the material with radicals generated thereupon can be cooled below room temperature and stored for some time at the cooled temperature (e.g., more than one hour, more than one day, more the one month or even more than one year), thawed, and then heated to a temperature above room temperature.

Figure 5:
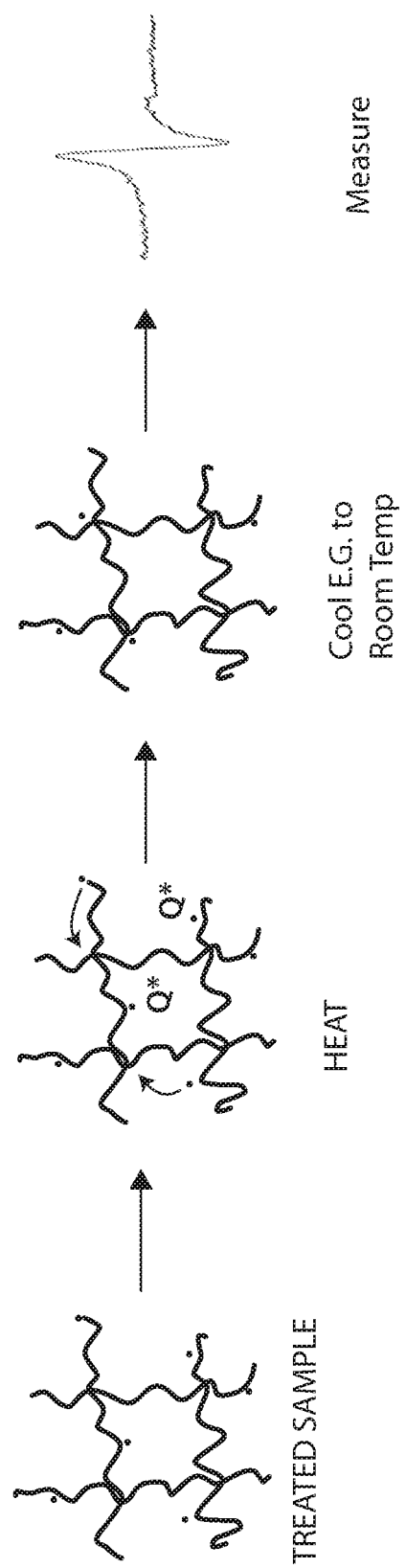
FIG. 5 is another schematic representation of the formation and quenching of radicals and the detection of the final quenched material.

A preferred embodiment is shown with reference to FIG. 5. The irradiated biomass is treated producing electrons on the biomass. The biomass (e.g., a sample of the biomass) is then heated for a time sufficient to quench, indicated as Q* in FIG. 5, some of the radicals and/or allow other radicals to migrate to more stable sites, indicated by the curved arrows. The sample is then cooled to freeze the radicals in place, for example, to room temperature. The sample can then be measured, e.g., by ESR, or stored for later processing. It should be noted that the cooling after heating need not be below room temperature although it can be. For example the sample can be cooled to about room temperature and then the ESR spectra can be measured. Alternatively, the ESR measurement can be done at a low temperatures (e.g. below about 0 deg C., below about −10 deg C., below about −20 deg C., below about −30 deg C., below about −40 deg C., below about −50 deg C., below about −60 deg C., below about −70 deg C., below about −80 deg C., below about −90 deg C., below about −100 deg C., below −120 deg C., below −140 deg C., below −160 deg C., below −180 deg C. or even below −200 deg C.). Before or after measuring the sample, or before or after heating the sample is preferably stored at a low temperature such as previously described to freeze the radicals. It is most preferred that if a sample is treated it is immediately (e.g., within a day) stored at a low temperature unless it will be measured by ESR.

Examples

ESR Spectra of Some Representative Compounds

Figure 6:
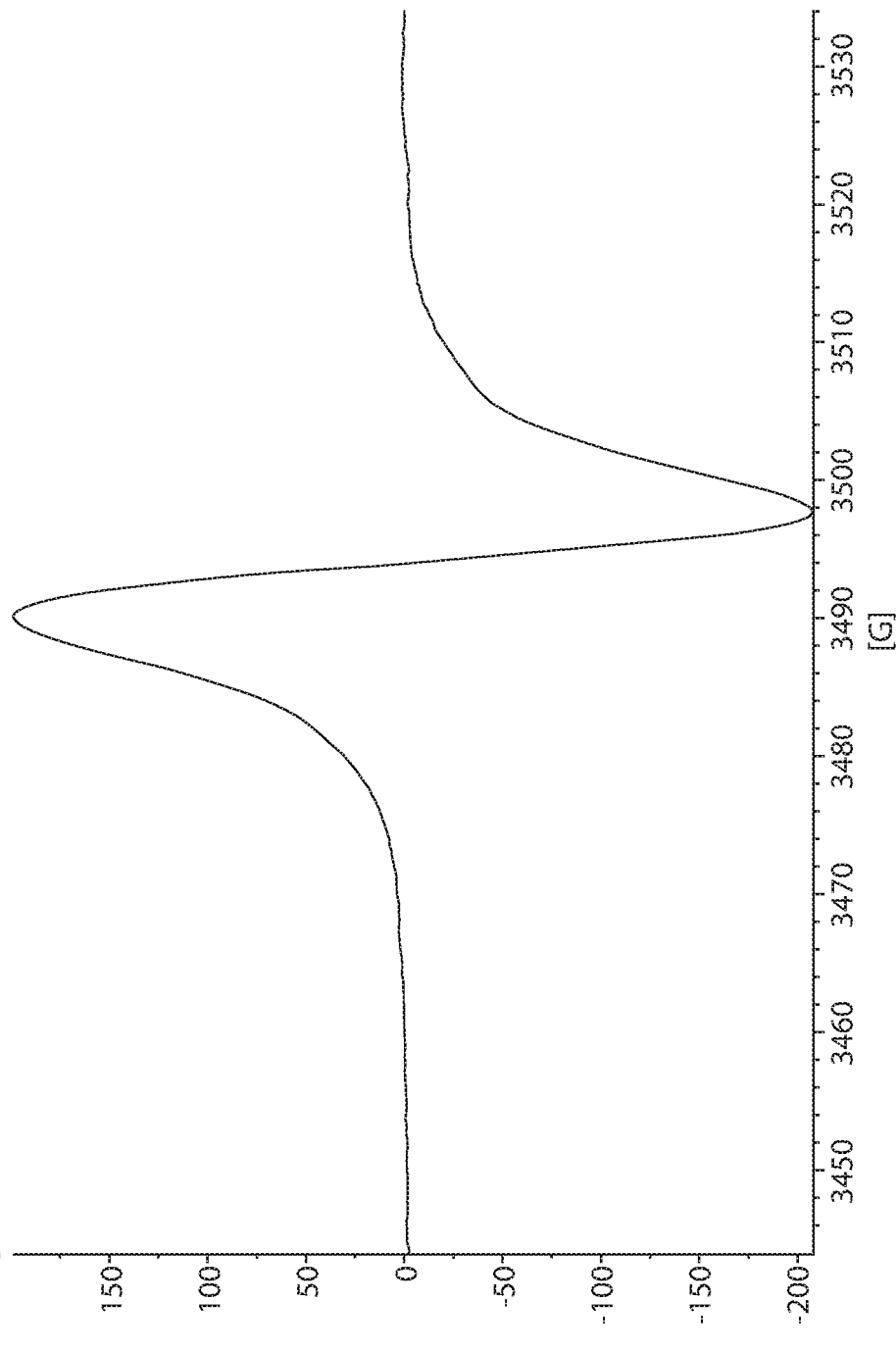
FIG. 6 shows a plot of an EPR spectrum of irradiated lignin.
Figure 7:
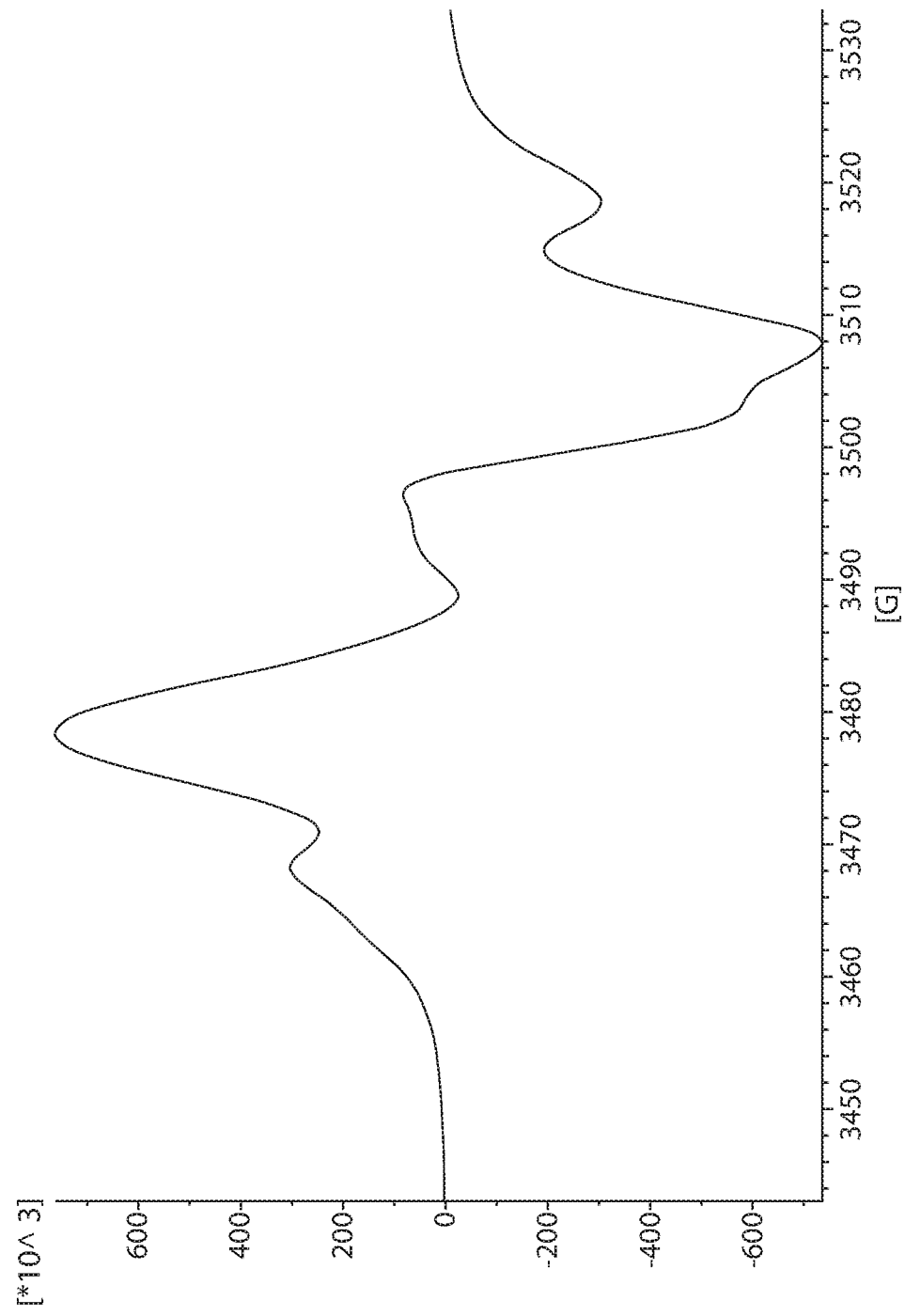
FIG. 7 shows a plot of an EPR spectrum of irradiated glucose.
Figure 8:
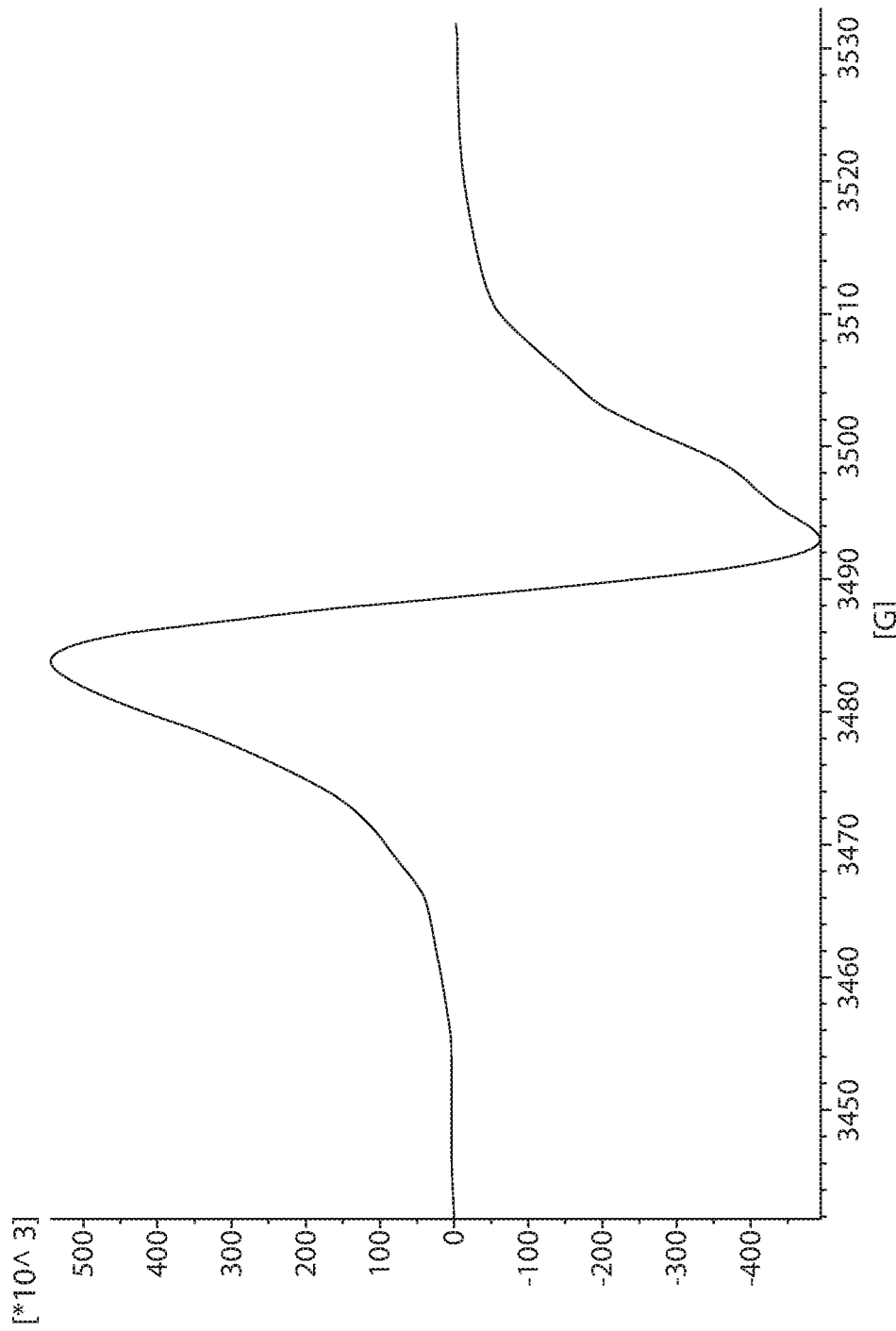
FIG. 8 shows a plot of an EPR spectrum of irradiated xylan.
Figure 9:
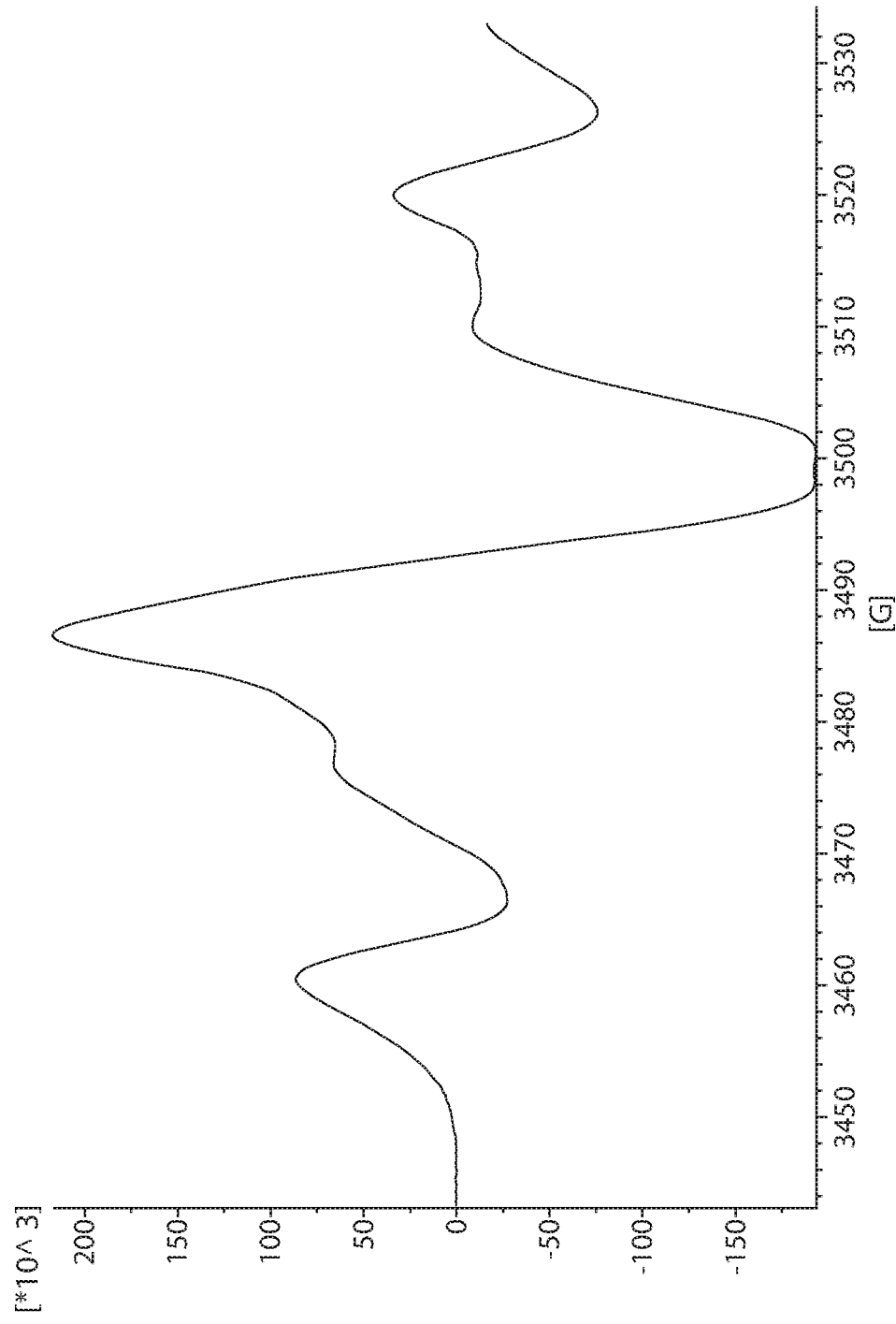
FIG. 9 shows a plot of an EPR spectrum of irradiated cellulose.
Figure 10:
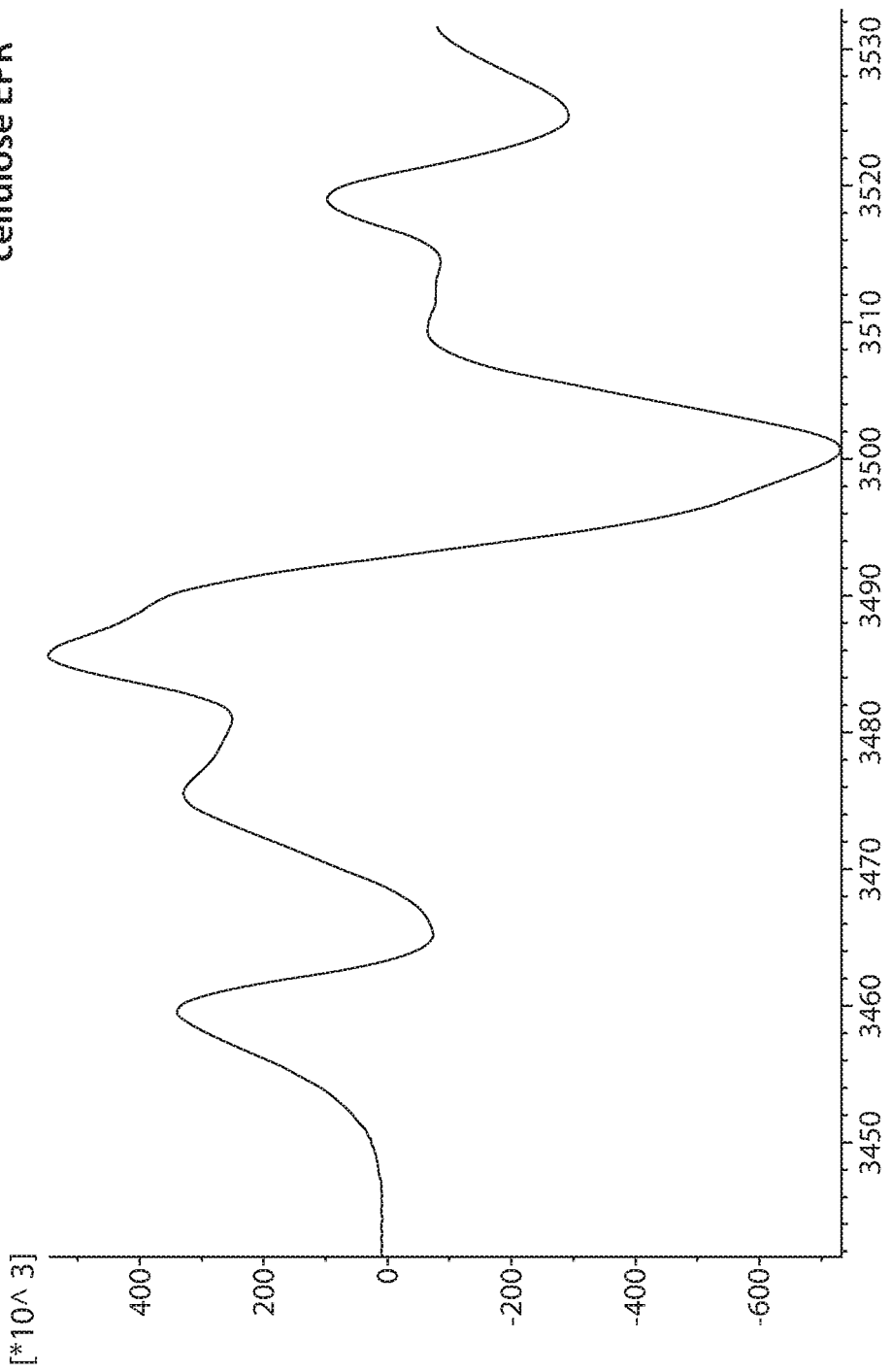
FIG. 10 shows a plot of an EPR spectrum of irradiated microcrystalline cellulose.
Figure 11:
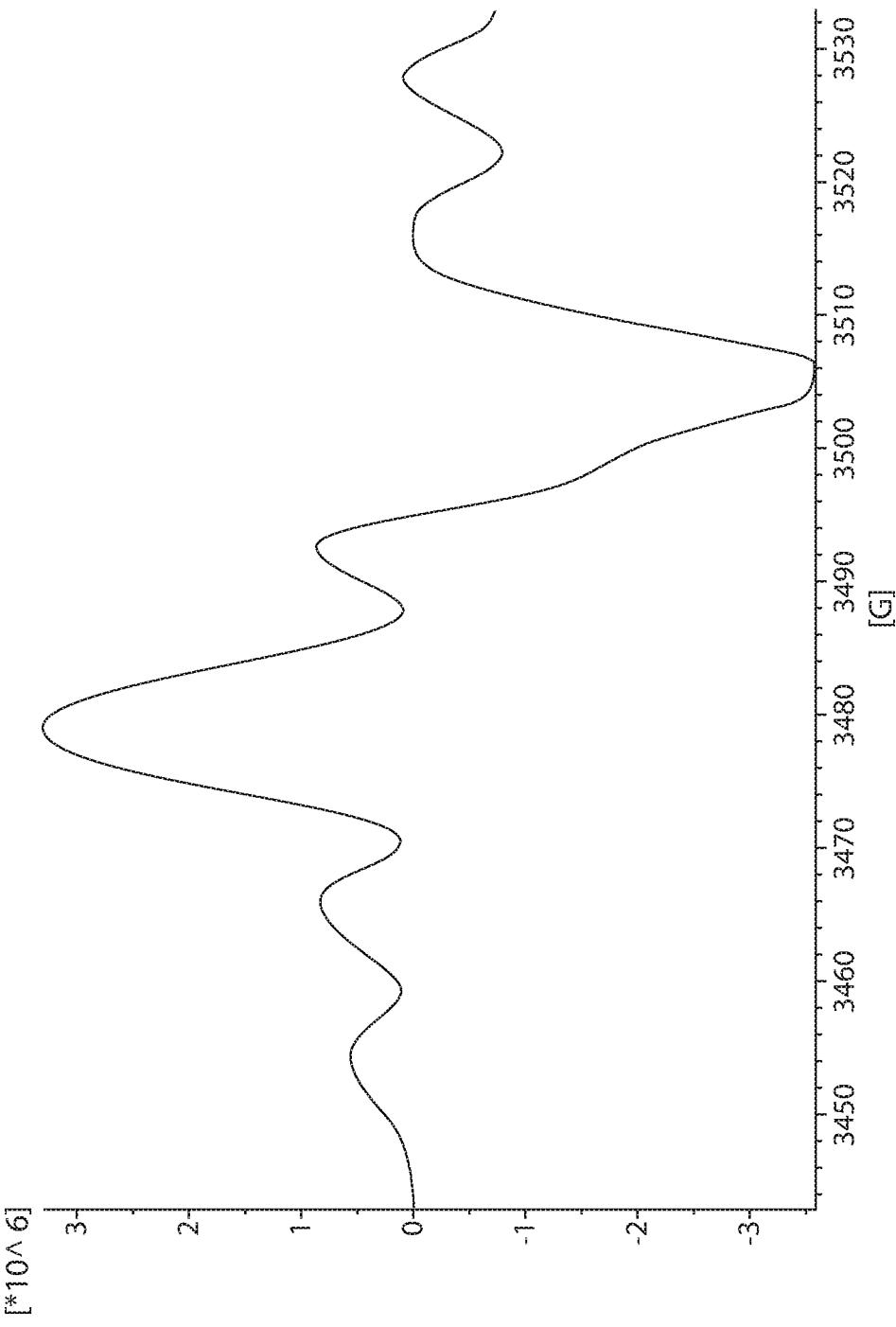
FIG. 11 shows a plot of an EPR spectrum of irradiated cellobiose.
Figure 12:
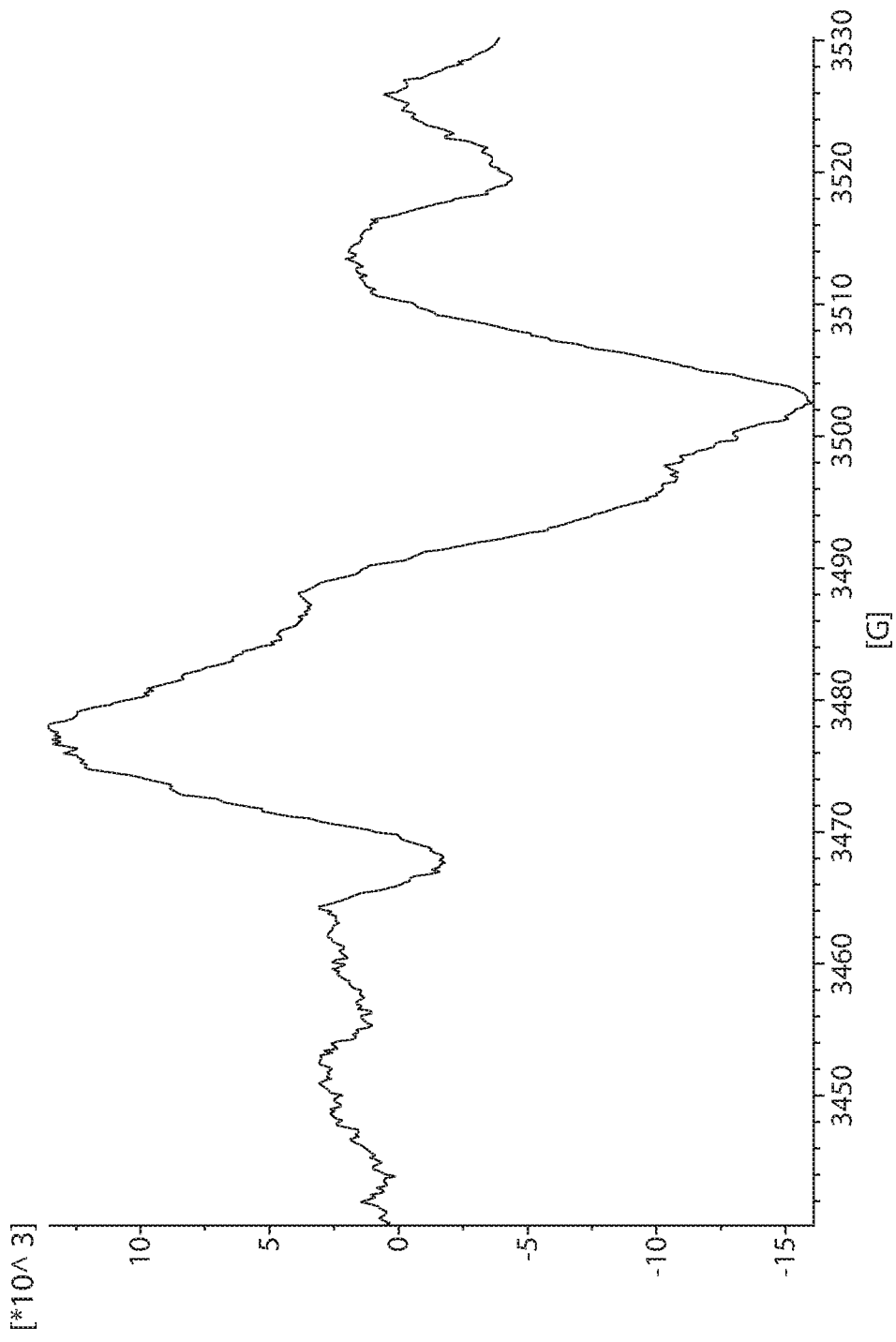
FIG. 12 shows a plot of an EPR spectrum of irradiated starch.

Samples obtained from commercial sources were irradiated with 20 Mrad of electron beam irradiation. These were then measured by EPR. A Bruker e-scan EPR spectrometer was used for the experiment. This kind of instrument is designed to perform routine X-band EPR measurements. The field sweep maximum is 3000 Gauss and is centered at about the g=2 resonance position. An EPR spectrum of irradiated Lignin is shown in FIG. 6. Irradiated glucose is shown in FIG. 7. Irradiated xylan is shown in FIG. 8. Irradiated cellulose is shown in FIG. 9. Irradiated microcrystalline cellulose is show in FIG. 10. Irradiated cellobiose is shown in FIG. 11. Irradiated starch is shown in FIG. 12.

EPR Selected Response Method

Figure 13:
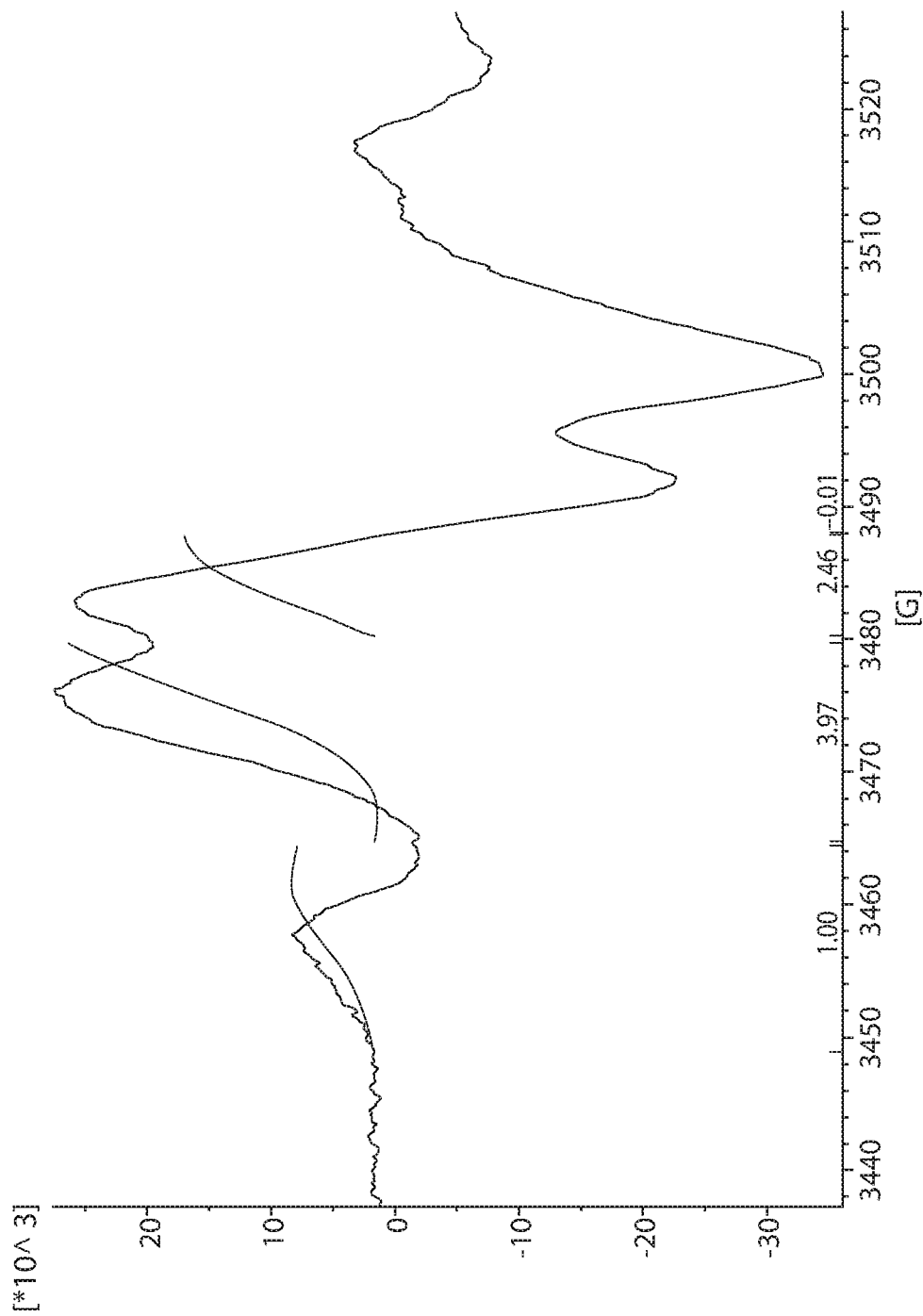
FIG. 13 shows a plot of an EPR spectrum of an irradiated and heat treated corn cob material showing the integrated peaks.

The EPR signal in this method is analyzed prior to integration. In particular, irradiation of corn cob material produces several radicals that can be attributed to speciation among the different components (e.g., carbohydrates, lignin, protein). Three signals or peaks can be resolved easily after heating using the heat treatment described above. A signal designated radical 1 (3478 G, 2.0048) is primarily or at least confounded with signals from lignin based radicals and other paramagnetic species such as Mn ions. Lignin radicals are relatively stable to heat treatment. Radicals 2 and 3 are primarily cellulose based and are also relatively stable to the heat treatment. Radical 2 occurs at 3470G, g=2.0088 while radical 3 occurs at 3452 and g=2.0186. Starch generates essentially no significant signal. Carbohydrates such as xyloglucan, glucomannan, xylan and dextran are relatively unstable to heat treatment. FIG. 13 is the EPR spectrum of an irradiated and heat treated corn cob material showing the integrated peaks.

Figure 14A:
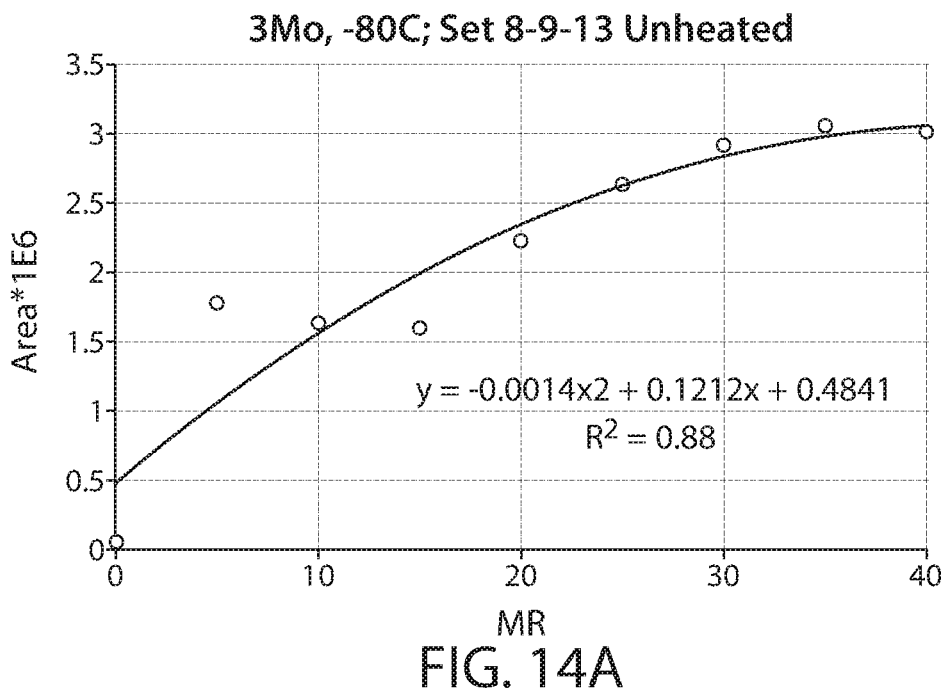
FIG. 14A shows a plot of an integrated response of a radical on irradiated biomass as measured by EPR vs. irradiation dose for non-heat treated sample.
Figure 14B:
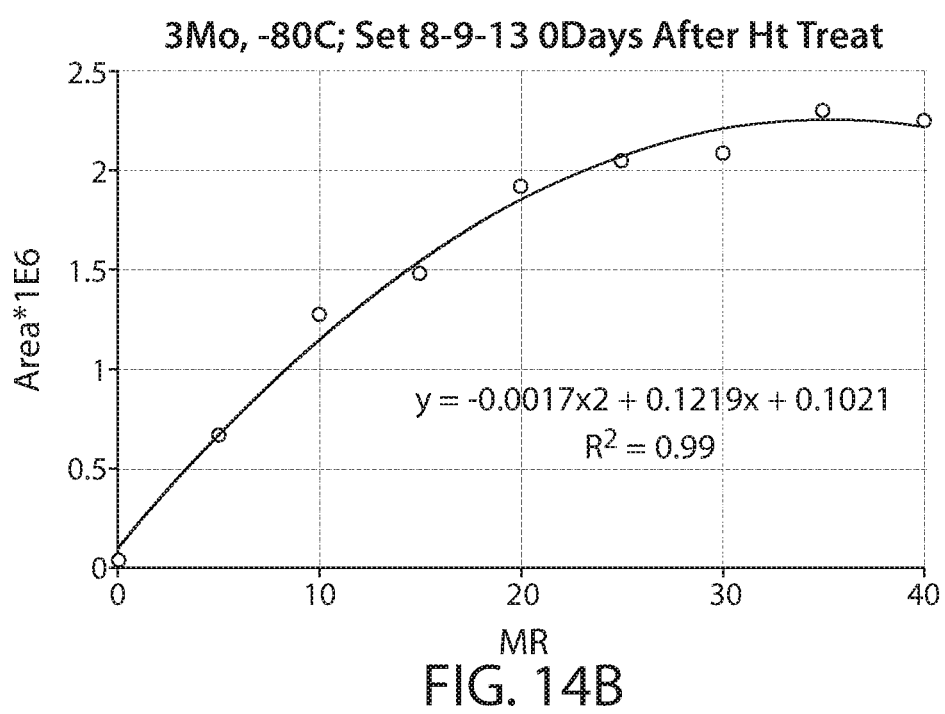
FIG. 14B shows a plot of an integrated response of a radical on irradiated biomass measured by EPR vs. irradiation dose for a heat treated sample.

Particulate corn cob biomass was irradiated with 5, 10, 15, 20, 25, 30, 35 and 40 Mrad of electron beam irradiation. The samples were stored for 3 months at −80 deg C. after the irradiation. The EPR response of samples after thawing them out was then measured. A carefully consistent sampling technique was utilized, using approximately 0.5 mL/250 mg of material in the EPR tube. The samples were then heated to 80 deg C. for 30 min and the EPR response was measured a second time. A plot of the Radical 2 integrated response vs irradiation dose for non-heat treated sample is shown by FIG. 14A while the corresponding heated sample is shown by FIG. 14B. A polynomial curve is fit to the plots. The correlation for the non-heat treated sample where $R^2$=0.88 is lower than the polynomial fit for the heat treated sample with $R^2$=0.991.

EPR Total Response Method

Particulate corn cob biomass was treated by electron beam irradiation at 5, 10, 15, 20, 25, 30, 35, and 40 Mrad. The samples were stored for 3 months at −80 deg C. after which they were thawed and heat treated at 80 deg C. for 30 min. Samples were packed into an EPR sample tube utilizing a vortex mixer. The EPR response for each sample was then measured as previously described. Each sample was run in triplicate with 4 scans per sample.

Figure 15:
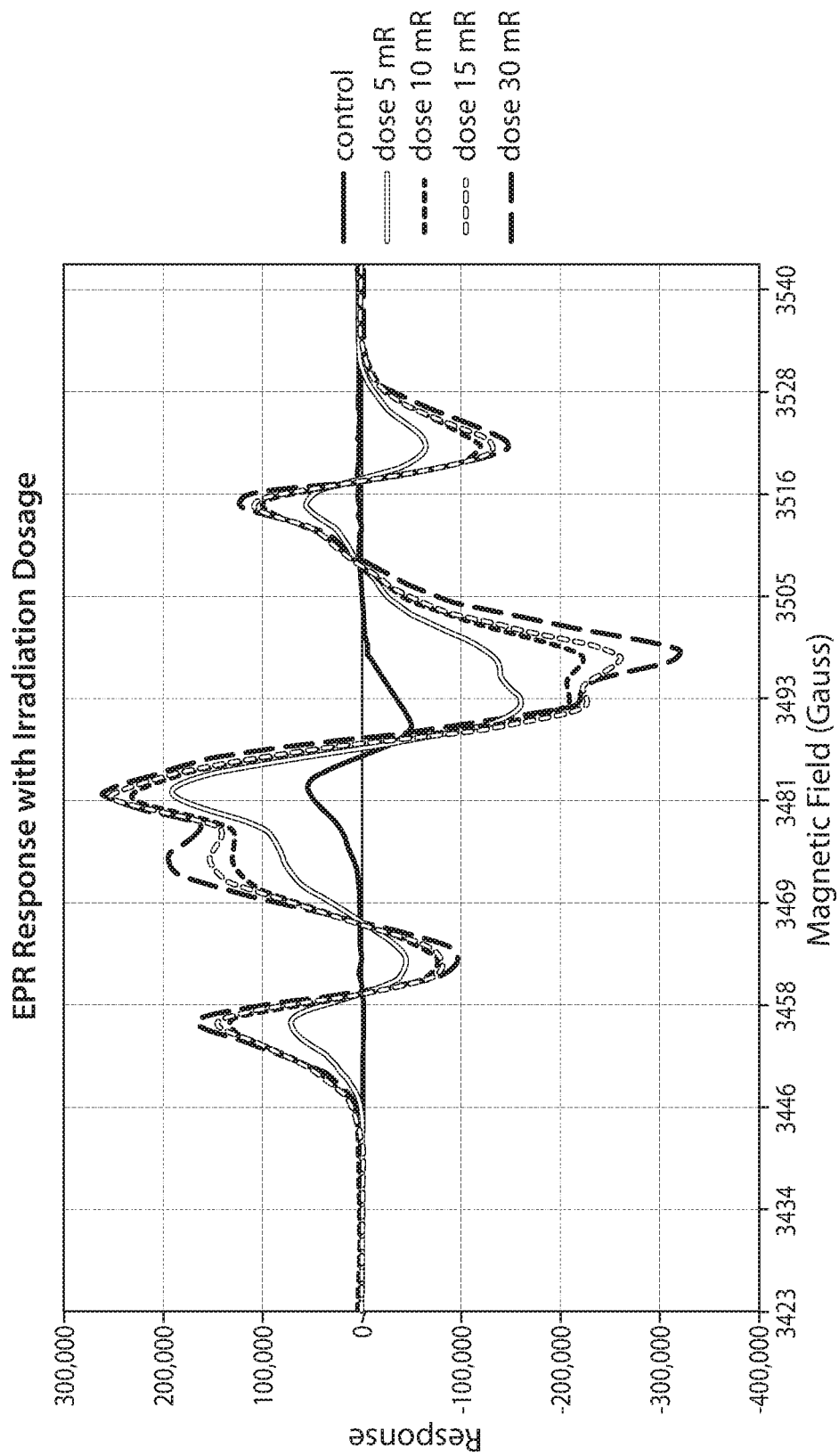
FIG. 15 shows a plot of an EPR spectrum of irradiated corn cob at various dosages.
Figure 16:
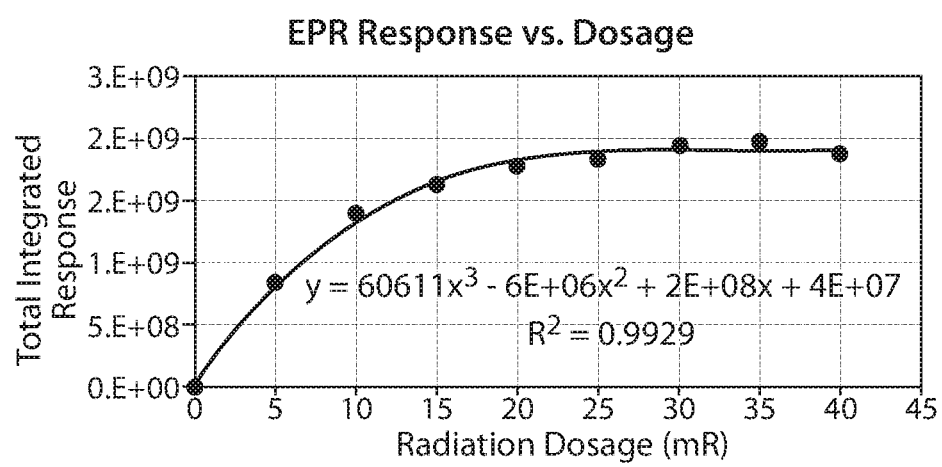
FIG. 16 shows a plot of the total integrated response of the radicals on irradiated biomass measured by EPR vs. irradiation dose.

The EPR spectra of several of the samples is shown as an overlay in FIG. 15. The signal increase from the lowest dose to the highest dose is consistent with a higher concentration of radicals on the biomass. The total integrated response corresponding to radicals 1, 2 and 3 was calculated and plotted against the dosage, as shown as FIG. 16. The plot shows a saturation response indicating that the maximum amount of radicals are formed at a dosage greater than about 20 Mrad.

ESR Spectra of Heated Biomass Material

Particulate corn cob biomass was treated by electron beam irradiation. The particulated biomass was loaded into polyethylene bags. The bags were placed onto a surface to form a ¾" thick layer of corn cob material. The material was irradiated on one side, then flipped over and irradiated on the other side. The conditions of irradiation are listed in Table 2. Samples were packed into an EPR sample tube utilizing a vortex mixer. The EPR response for each sample was then measured as previously described. Each sample was run in triplicate with 4 scans per sample.

TABLE 2

Corn Cob Irradiation Conditions

| Sample | Weight (g) | Energy (Mev) | Dose Total (Mrad) |
|---|---|---|---|
| 1 | 130 g | 0.8 MeV | 25 |
| 2 | 130 g | 0.8 MeV | 30 |
| 3 | 130 g | 0.8 MeV | 35 |
| 4 | 130 g | 1.0 MeV | 25 |
| 5 | 130 g | 1.0 MeV | 30 |
| 6 | 130 g | 1.0 MeV | 35 |
| 7 | 130 g | 3 MeV | 35 |

Figure 17:
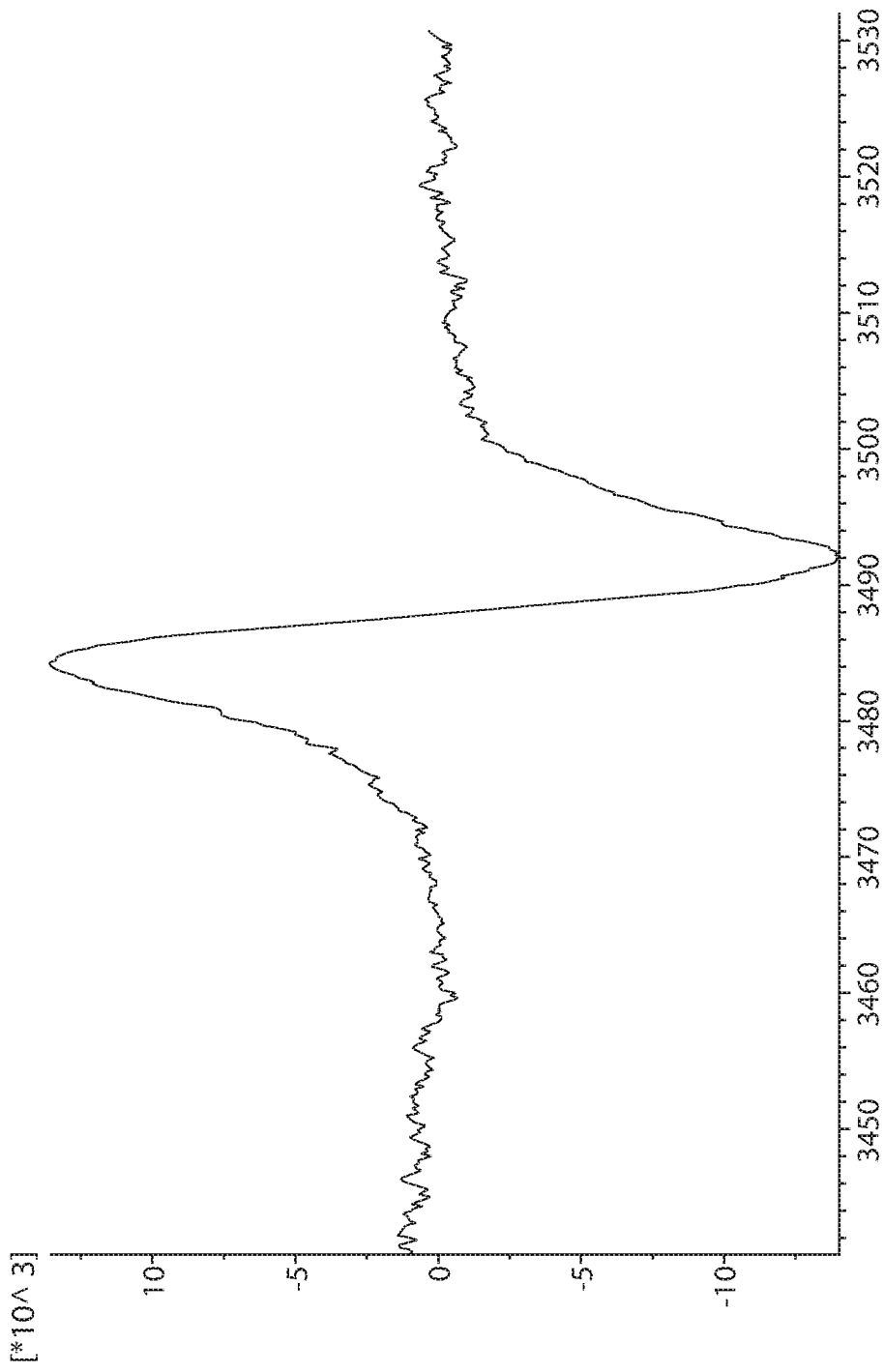
FIG. 17 shows a plot of an EPR spectrum of non-irradiated corn cob.
Figure 18:
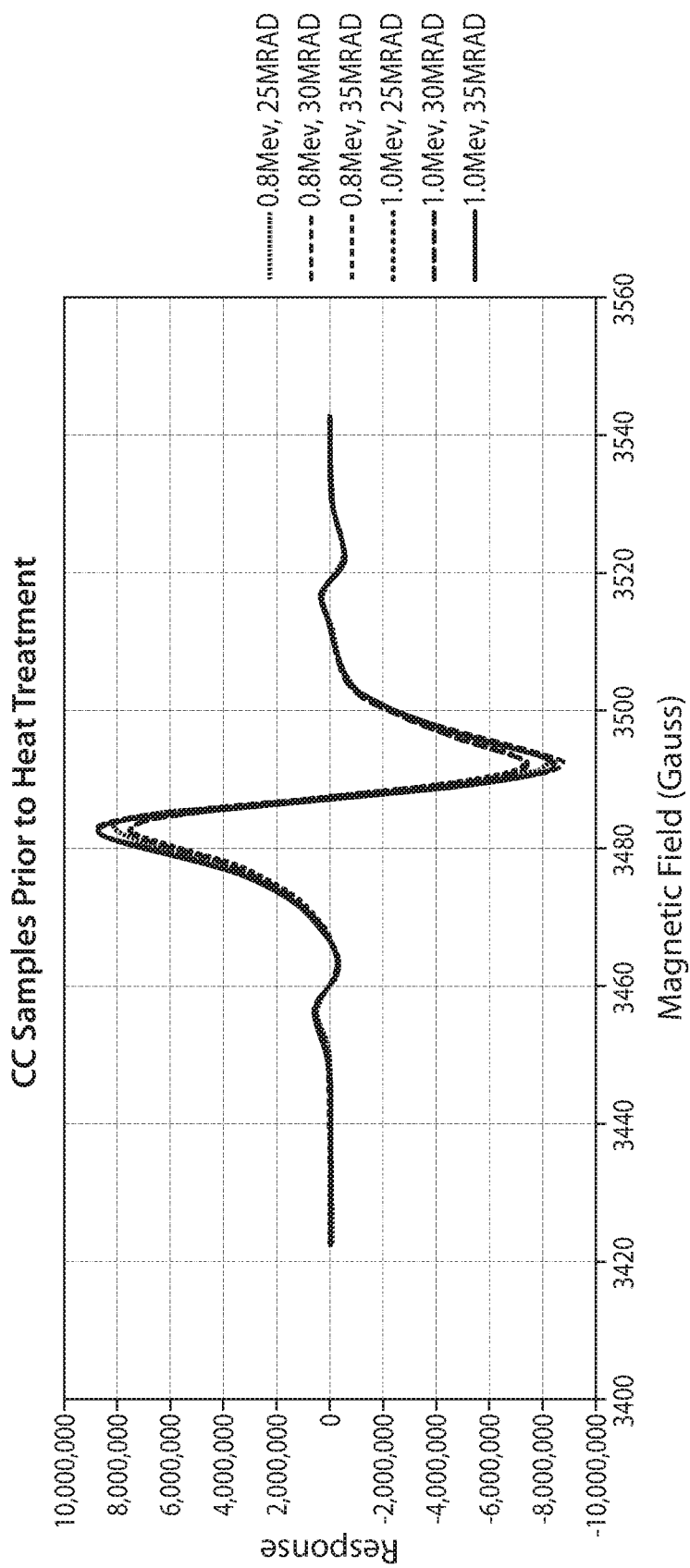
FIG. 18 shows a plot of 6 EPR spectra of irradiated corn cob at different electron energies and dosages without a sample heat treatment.
Figure 19:
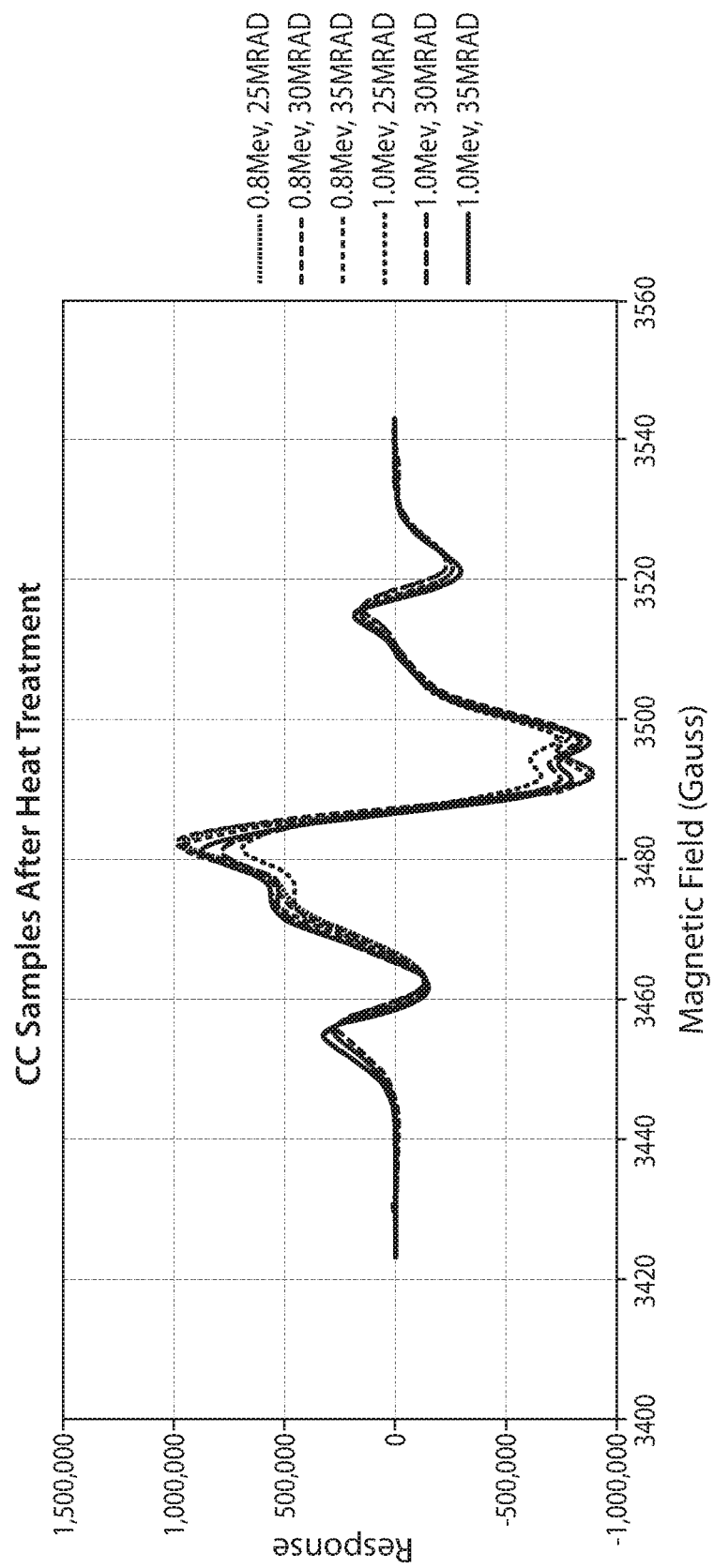
FIG. 19 shows a plot of 6 EPR spectra of irradiated corn cob at different electron energies and dosages after a sample heat treatment.

A plot of the EPR spectrum of non-irradiated corn cob biomass is shown in FIG. 17. FIG. 18 is a plot of the EPR spectrum of samples 1 through 6 without heat treatment. FIG. 19 shows the EPR spectrum of samples 1-6 after a heat treatment of 80 deg C. for 30 min. Heat treatment shows a decrease in total response by about 80 to 90%, as well as changing the shape of the response. These two effects are consistent with quenching of different types of radicals to different degrees and possibly with the migration of radicals of high energy to sites with higher stability, such as lignin sites.

Figure 20:
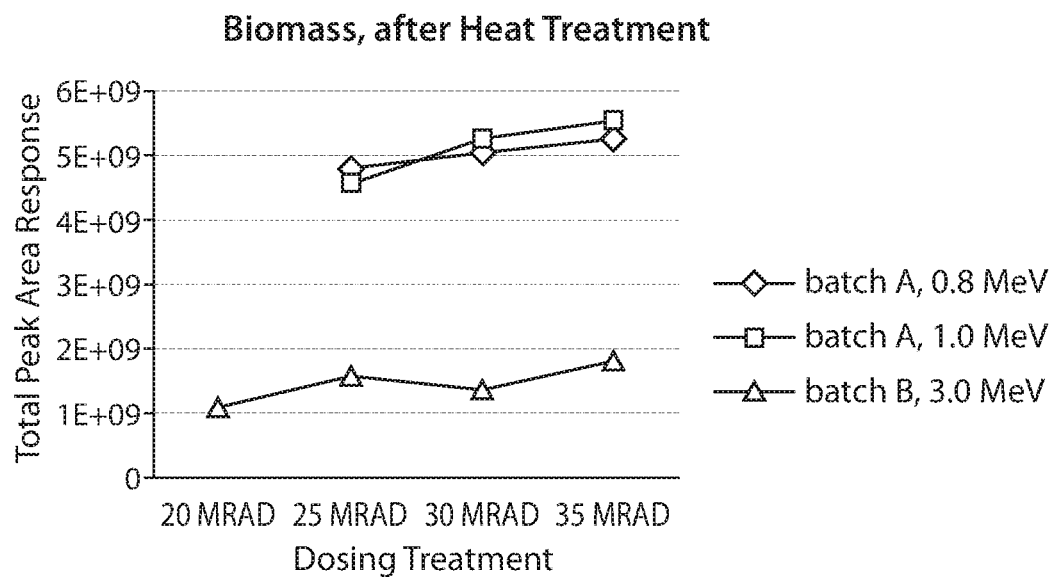
FIG. 20 shows a plot of the total integrated EPR response for a biomass material where the treatment is with electrons of different energies and for different dosages.

A plot of the total integrated EPR response is shown in FIG. 20 for samples 1-7 after heat treatment. It is noted that the treatment with 3 MeV electrons appears to produce a lower EPR response. This result appears to be consistent with the higher energy electrons not being as effective in producing stable radicals in the biomass material. One possible reason is that at the higher energies the electrons penetrate through the sample, e.g., to the support surface. In addition to not producing radicals in the biomass, the heating of the surface may cause quenching of the radicals and/or decomposition of the biomass material.

EPR Verification and Measurement Method

Analysis of irradiated materials may be performed for the purposes of verifying the irradiation exposure level (i.e., EPR dose) and for obtaining measurement data. Correlating exposure level (dose) with EPR has previously been performed for the purposes of monitoring the level of ionizing irradiation in foods, as described by Polovka, Brezova, Simko (2007) *J. Food Nut. Res.* 46:75-83, herein incorporated by reference.

Four different examples of calibration standard materials that were used for purposes of verification are listed below in Table 3.

TABLE 3

Example Calibration Standards

| Material | Manufacturer/Supplier | Grade | Catalog No. |
|---|---|---|---|
| BDPA (bis(diphenylene)-2-phenylallyl) | Bruker | Certified | ER-213-BDS |
| Strong pitch | Bruker | Certified | ER-213-SPS |
| Untreated corncob (sized at 14/40 mesh) | Various | Research | N/A |
| Irradiated corncob calibration standards* | E-Beam or other | Research | N/A |

*Stored in screw capped tubes at −80 degrees C.

A reference irradiated corncob material was obtained by treating particulate corn cob biomass with electron beam irradiation at 5, 10, 15, 20, 25, 30, 35, and 40 Mrad. A calibration curve using these results (plotting radiation dosage vs. response) was then constructed. See for example, FIG. 16. Further details related to obtaining this measurement data are discussed below.

Sample sizes of 2 mL from each calibration standard were transferred to a clean, dry 15 mL tube and tightly closed with a screw cap. These tubes were then placed into an autoclave envelope and laid flat for 30 minutes in a pre-heated oven set at 85±5 degrees C. The envelope was removed from the oven and the samples were allowed to cool to room temperature. The heat-treated contents of each tube were then mixed by shaking the tube. Test samples were also prepared according to this procedure.

A Bruker e-scan EPR spectrometer as described above was used to obtain the measurement results. The EPR spectrometer was powered on for at least 30 minutes and was set to the parameters listed below in Table 4.

TABLE 4

EPR Instrumentation Analysis Settings

| Parameter | Set Value |
|---|---|
| Microwave frequency | 9.76 GHz |
| Modulation frequency | 86 kHz |
| Modulation Amplitude | 3.28 G |
| Microwave Power | 90 µW |
| Sweep Width | 120 G |
| Sweep Time | 41.9 s |
| Center Field | 3482 G |
| Conversion Time | 81.9 ms |
| Time Constant | 328 ms |
| Phase | 1.03 deg |
| Receiver Gain | 224 |
| Resolution | 512 |
| Number of X-Scans | 4 |

The BDPA standard was run in triplicate to assure that a strong narrow signal with a band maximum value of 3496.8±2 G was obtained. If this was not obtained, then instrument equilibration and/or calibration was re-verified and, if necessary, a recalibration was performed. The same procedure was performed on the Strong Pitch sample (3491.8+/−2 G).

Samples for the EPR spectrometer were prepared by first filling the EPR test tube to at least a level that corresponded with a pre-marked 2 inch line. Sample test tubes were then wiped to minimize contamination, placed into the instrument and measured. Data collection also included running measurements on a blank empty tube for purposes of verifying a negligible signal. The corncob calibration standards were run from lowest to highest in dose concentration.

Software, such as WinEPR (Bruker), may be used for acquiring and processing measurement data from the EPR spectrometer. The results from the calibration standards listed above in Table 3 were plotted (radiation dosage vs. response or total integrated area) using suitable graphical software, such as Microsoft Excel. The measurement curves were fitted with a third degree polynomial and the resulting equation and correlation coefficient ($R^2$) was obtained, such as represented by the measurement data shown in FIG. 16. Plotted results with an $R^2$ value of at least 0.95 were determined to be acceptable.

Effect of Heat Treatment on Saccharification of Biomass

Particulate corn cob biomass was treated by electron beam irradiation at 5, 20, 35 and 40 Mrad. Samples from each irradiation level were partitioned into two portions. One portion was saccharified directly while the other portion was heated at 80 deg C. for 30 min prior to saccharification. Saccharifications were performed utilizing cellulase enzymes and all saccharifications were done using similar conditions. The concentration of the sugars glucose, fructose and xylose (g/L) in the saccharified samples was determined utilizing HPLC. The % yield of total sugars as a weight % was also calculated. The heat treatment did not appear to have any effect on the overall saccharification yield or any of the individual monosaccharide amounts. The results from the irradiations are listed in Table 5. In addition, the total integrated EPR response for heat treated materials is listed in Table 5.

TABLE 5

Irradiation/Heat Saccharification Results Summary

| DOSE (Mrad) | Heat Treatment? | Glucose (g/L) | Xylose (g/L) | Fructose (g/L) | Total Sugars wt % | EPR Total integrated Response |
|---|---|---|---|---|---|---|
| 0 | No | 23.3 | 14.8 | 3.0 | 19.6 | — |
| 0 | Yes | 22.9 | 14.3 | 3.2 | 19.2 | 0 |
| 5 | No | 33.2 | 18.3 | 5.0 | 26.9 | — |
| 5 | Yes | 33.0 | 18.3 | 4.9 | 26.8 | 8.36E+08 |
| 20 | No | 39.2 | 27.8 | 4.4 | 34.0 | — |
| 20 | Yes | 38.4 | 27.3 | 4.5 | 33.4 | 1.771E+09 |
| 35 | No | 44.1 | 34.1 | 2.4 | 38.4 | — |
| 35 | Yes | 43.9 | 34.0 | 2.5 | 38.2 | 1.967E+09 |
| 40 | No | 42.1 | 33.8 | 3.4 | 37.7 | — |
| 40 | Yes | 41.8 | 33.6 | 3.3 | 37.5 | 1.859E+09 |

Figure 21:
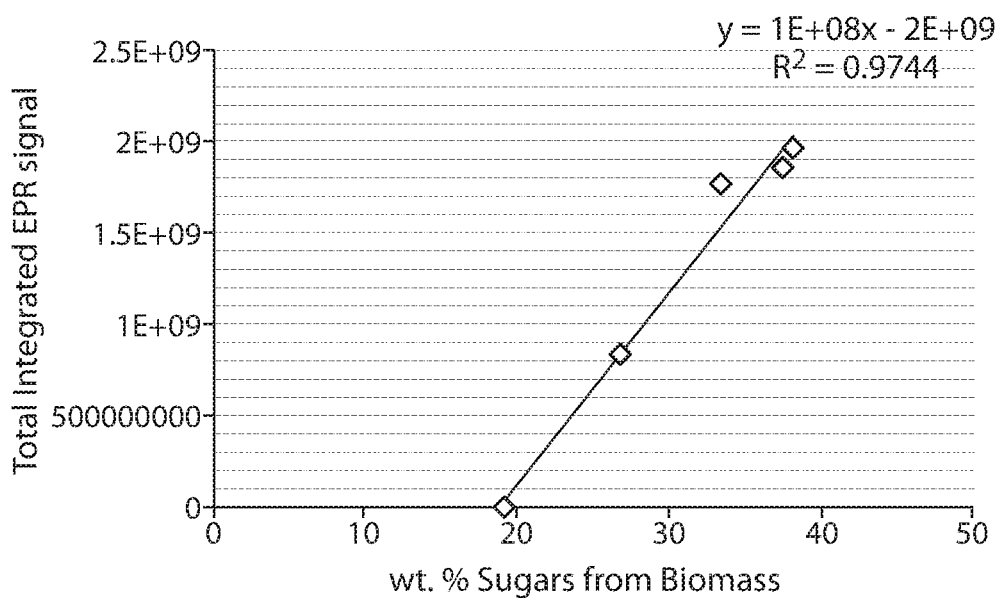
FIG. 21 shows a plot of the total wt % sugar yield vs. the total integrated response of an EPR of an irradiated lignocellulosic material.

The total wt % sugar yield vs the total integrated response is shown in FIG. 21. The plot shows a high correlation, $R^2=0.9744$, between the total integrated response and the total sugars.

Radiation Treatment

As discussed above, the feedstock, such as a lignocellulosic or cellulosic material, can be treated with radiation to modify its structure to reduce its recalcitrance. Such treatment can, for example, reduce the average molecular weight of the feedstock, change the crystalline structure of the feedstock, and/or increase the surface area and/or porosity of the feedstock. Radiation can be performed by, for example electron beam, ion beam, 100 nm to 28 nm ultraviolet (UV)

light, gamma or X-ray radiation. Radiation treatments and systems for treatments are discussed in U.S. Pat. No. 8,142,620 and U.S. patent application Ser. No. 12/417,731, the entire disclosures of which are incorporated herein by reference.

Each form of radiation ionizes the biomass via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, *neptunium*, curium, californium, americium, and plutonium. Electrons interact via Coulomb scattering and bremsstrahlung radiation produced by changes in the velocity of electrons.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired to change the molecular structure of the carbohydrate containing material, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 atomic units.

Gamma radiation has the advantage of a significant penetration depth into a variety of material in the sample.

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has an energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

Electron bombardment may be performed using an electron beam device that has a nominal energy of less than 10 MeV, e.g., less than 7 MeV, less than 5 MeV, or less than 2 MeV, e.g., from about 0.5 to 1.5 MeV, from about 0.8 to 1.8 MeV, or from about 0.7 to 1 MeV. According to some implementations, the nominal energy is about 500 to 800 keV.

The electron beam may have a relatively high total beam power (the combined beam power of all accelerating heads, or, if multiple accelerators are used, of all accelerators and all heads), e.g., at least 25 kW, e.g., at least 30, 40, 50, 60, 65, 70, 80, 100, 125, or 150 kW. In some cases, the power is even as high as 500 kW, 750 kW, or even 1000 kW or more. In some cases the electron beam has a beam power of 1200 kW or more, e.g., 1400, 1600, 1800, or even 3000 kW.

This high total beam power is usually achieved by utilizing multiple accelerating heads. For example, the electron beam device may include two, four, or more accelerating heads. The use of multiple heads, each of which has a relatively low beam power, prevents excessive temperature rise in the material, thereby preventing burning of the material, and also increases the uniformity of the dose through the thickness of the layer of material.

It is generally preferred that the bed of biomass material has a relatively uniform thickness. In some embodiments the thickness is less than about 1 inch (e.g., less than about 0.75 inches, less than about 0.5 inches, less than about 0.25 inches, less than about 0.1 inches, between about 0.1 and 1 inch, between about 0.2 and 0.3 inches).

It is desirable to treat the material as quickly as possible. In general, it is preferred that treatment be performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 2 Mrad per second. Higher dose rates allow a higher throughput for a target (e.g., the desired) dose. Higher dose rates generally require higher line speeds, to avoid thermal decomposition of the material. In one implementation, the accelerator is set for 3 MeV, 50 mA beam current, and the line speed is 24 feet/minute, for a sample thickness of about 20 mm (e.g., comminuted corn cob material with a bulk density of 0.5 g/cm$^3$).

In some embodiments, electron bombardment is performed until the material receives a total dose of at least 0.1 Mrad, 0.25 Mrad, 1 Mrad, 5 Mrad, e.g., at least 10, 20, 30 or at least 40 Mrad. In some embodiments, the treatment is performed until the material receives a dose of from about 10 Mrad to about 50 Mrad, e.g., from about 20 Mrad to about 40 Mrad, or from about 25 Mrad to about 30 Mrad. In some implementations, a total dose of 25 to 35 Mrad is preferred, applied ideally over a couple of passes, e.g., at 5 Mrad/pass with each pass being applied for about one second. Cooling methods, systems and equipment can be used before, during, after and in between radiations, for example utilizing a cooling screw conveyor and/or a cooled vibratory conveyor.

Using multiple heads as discussed above, the material can be treated in multiple passes, for example, two passes at 10 to 20 Mrad/pass, e.g., 12 to 18 Mrad/pass, separated by a few seconds of cool-down, or three passes of 7 to 12 Mrad/pass, e.g., 5 to 20 Mrad/pass, 10 to 40 Mrad/pass, 9 to 11 Mrad/pass. As discussed herein, treating the material with several relatively low doses, rather than one high dose, tends to prevent overheating of the material and also increases dose uniformity through the thickness of the material. In some implementations, the material is stirred or otherwise mixed during or after each pass and then smoothed into a uniform layer again before the next pass, to further enhance treatment uniformity.

In some embodiments, electrons are accelerated to, for example, a speed of greater than 75 percent of the speed of light, e.g., greater than 85, 90, 95, or 99 percent of the speed of light.

In some embodiments, any processing described herein occurs on lignocellulosic material that remains dry as acquired or that has been dried, e.g., using heat and/or reduced pressure. For example, in some embodiments, the cellulosic and/or lignocellulosic material has less than about 25 wt % retained water, measured at 25° C. and at fifty percent relative humidity (e.g., less than about 20 wt %, less than about 15 wt %, less than about 14 wt %, less than about 13 wt %, less than about 12 wt %, less than about 10 wt %, less than about 9 wt %, less than about 8 wt %, less than about 7 wt %, less than about 6 wt %, less than about 5 wt %, less than about 4 wt %, less than about 3 wt %, less than about 2 wt %, less than about 1 wt %, or less than about 0.5 wt %.

In some embodiments, two or more ionizing sources can be used, such as two or more electron sources. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light. The biomass is conveyed through the treatment zone where it can be bombarded with electrons.

It may be advantageous to repeat the treatment to more thoroughly reduce the recalcitrance of the biomass and/or further modify the biomass. In particular the process parameters can be adjusted after a first (e.g., second, third, fourth or more) pass depending on the recalcitrance of the material. In some embodiments, a conveyor can be used which includes a circular system where the biomass is conveyed multiple times through the various processes described above. In some other embodiments multiple treatment devices (e.g., electron beam generators) are used to treat the biomass multiple (e.g., 2, 3, 4 or more) times. In yet other embodiments, a single electron beam generator may be the source of multiple beams (e.g., 2, 3, 4 or more beams) that can be used for treatment of the biomass.

The effectiveness in changing the molecular/supermolecular structure and/or reducing the recalcitrance of the carbohydrate-containing biomass depends on the electron energy used and the dose applied, while exposure time depends on the power and dose. In some embodiments, the dose rate and total dose are adjusted so as not to destroy (e.g., char or burn) the biomass material. For example, the carbohydrates should not be damaged in the processing so that they can be released from the biomass intact, e.g. as monomeric sugars.

In some embodiments, the treatment (with any electron source or a combination of sources) is performed until the material receives a dose of at least about 0.05 Mrad, e.g., at least about 0.1, 0.25, 0.5, 0.75, 1.0, 2.5, 5.0, 7.5, 10.0, 15, 20, 25, 30, 40, 50, 60, 70, 80, 90, 100, 125, 150, 175, or 200 Mrad. In some embodiments, the treatment is performed until the material receives a dose of between 0.1-100 Mrad, 1-200, 5-200, 10-200, 5-150, 50-150 Mrad, 5-100, 5-50, 5-40, 10-50, 10-75, 15-50, 20-35 Mrad.

In some embodiments, relatively low doses of radiation are utilized, e.g., to increase the molecular weight of a cellulosic or lignocellulosic material (with any radiation source or a combination of sources described herein). For example, a dose of at least about 0.05 Mrad, e.g., at least about 0.1 Mrad or at least about 0.25, 0.5, 0.75. 1.0, 1.5, 2.0, 2.5, 3.0, 3.5, 4.0, or at least about 5.0 Mrad. In some embodiments, the irradiation is performed until the material receives a dose of between 0.1 Mrad and 2.0 Mrad, e.g., between 0.5 Mrad and 4.0 Mrad or between 1.0 Mrad and 3.0 Mrad.

In certain instances, it may also be desirable to irradiate from multiple directions, simultaneously, or sequentially, in order to achieve a desired degree of penetration of radiation into the material. For example, depending on the density and moisture content of the material, such as wood, and the type of radiation source used (e.g., gamma or electron beam), the maximum penetration of radiation into the material may be only about 0.75 inch. In such cases, a thicker section (up to 1.5 inch) can be irradiated by first irradiating the material from one side, and then turning the material over and irradiating from the other side. Irradiation from multiple directions can be particularly useful with electron beam radiation, which irradiates faster than gamma radiation, but typically does not achieve as great a penetration depth.

Radiation Opaque Materials

The invention can include processing a material (e.g., lignocellulosic or cellulosic feedstock) in a vault and/or bunker that is constructed using radiation opaque materials. In some implementations, the radiation opaque materials are selected to be capable of shielding the components from X-rays with high energy (short wavelength), which can penetrate many materials. One important factor in designing a radiation shielding enclosure is the attenuation length of the materials used, which will determine the required thickness for a particular material, blend of materials, or layered structure. The attenuation length is the penetration distance at which the radiation is reduced to approximately 1/e (e=Euler's number) times that of the incident radiation. Although virtually all materials are radiation opaque if thick enough, materials containing a high compositional percentage (e.g., density) of elements that have a high Z value (atomic number) have a shorter radiation attenuation length and thus if such materials are used, a thinner, lighter shielding can be provided. Examples of high Z value materials that are used in radiation shielding are tantalum and lead. Another important parameter in radiation shielding is the halving distance, which is the thickness of a particular material that will reduce gamma ray intensity by 50%. As an example for X-ray radiation with an energy of 0.1 MeV the halving thickness is about 15.1 mm for concrete and about 2.7 mm for lead, while with an X-ray energy of 1 MeV the halving thickness for concrete is about 44.45 mm and for lead is about 7.9 mm. Radiation opaque materials can be materials that are thick or thin so long as they can reduce the radiation that passes through to the other side. Thus, if it is desired that a particular enclosure have a low wall thickness, e.g., for light weight or due to size constraints, the material chosen should have a sufficient Z value and/or attenuation length so that its halving length is less than or equal to the desired wall thickness of the enclosure.

In some cases, the radiation opaque material may be a layered material, for example having a layer of a higher Z value material, to provide good shielding, and a layer of a lower Z value material to provide other properties (e.g., structural integrity, impact resistance, etc.). In some cases, the layered material may be a "graded-Z" laminate, e.g., including a laminate in which the layers provide a gradient from high-Z through successively lower-Z elements. In some cases the radiation opaque materials can be interlocking blocks, for example, lead and/or concrete blocks can be supplied by NELCO Worldwide (Burlington, Mass.), and reconfigurable vaults can be utilized.

A radiation opaque material can reduce the radiation passing through a structure (e.g., a wall, door, ceiling, enclosure, a series of these or combinations of these) formed of the material by about at least about 10%, (e.g., at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%) as compared to the incident radiation. Therefore, an enclosure made of a radiation opaque material can reduce the exposure of equipment/system/components by the same amount. Radiation opaque materials can include stainless steel, metals with Z values above 25 (e.g., lead, iron), concrete, dirt, sand and combinations thereof. Radiation opaque materials can include a barrier in the direction of the incident radiation of at least about 1 mm (e.g., 5 mm, 10 mm, 5 cm, 10 cm, 100 cm, 1 m and even at least about 10 m).

Radiation Sources

The type of radiation used for treating a feedstock (e.g., a lignocellulosic or cellulosic material) determines the kinds of radiation sources used as well as the radiation devices and associated equipment. The methods, systems and equipment described herein, for example, for treating materials with radiation, can utilize sources as described herein as well as any other useful source.

Sources of gamma rays include radioactive nuclei, such as isotopes of cobalt, calcium, technetium, chromium, gallium, indium, iodine, iron, krypton, samarium, selenium, sodium, thallium, and xenon.

Sources of X-rays include electron beam collision with metal targets, such as tungsten or molybdenum or alloys, or compact light sources, such as those produced commercially by Lyncean.

Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, *neptunium*, curium, californium, americium, and plutonium.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Accelerators used to accelerate the particles can be electrostatic DC, electrodynamic DC, RF linear, magnetic induction linear or continuous wave. For example, cyclotron type accelerators are available from IBA, Belgium, such as the RHODOTRON™ system, while DC type accelerators are available from RDI, now IBA Industrial, such as the DYNAMITRON®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria.

Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, which are then accelerated through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scanned magnetically in the x-y plane, where the electrons are initially accelerated in the z direction down the accelerator tube and extracted through a foil window. Scanning the electron beams is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, Van de Graaff accelerators, and folded tandem accelerators. Such devices are disclosed, for example, in U.S. Pat. No. 7,931,784 to Medoff, the complete disclosure of which is incorporated herein by reference.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of carbohydrate-containing materials, for example, by the mechanism of chain scission. In addition, electrons having energies of 0.5-10 MeV can penetrate low density materials, such as the biomass materials described herein, e.g., materials having a bulk density of less than 0.5 g/cm$^3$, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV. Methods of irradiating materials are discussed in U.S. Pat. App. Pub. 2012/0100577 A1, filed Oct. 18, 2011, the entire disclosure of which is herein incorporated by reference.

Electron beam irradiation devices may be procured commercially from Ion Beam Applications, Louvain-la-Neuve, Belgium, NHV Corporation, Japan or the Titan Corporation, San Diego, Calif. Typical electron energies can be 0.5 MeV, 1 MeV, 2 MeV, 4.5 MeV, 7.5 MeV, or 10 MeV. Typical electron beam irradiation device power can be 1 kW, 5 kW, 10 kW, 20 kW, 50 kW, 60 kW, 70 kW, 80 kW, 90 kW, 100 kW, 125 kW, 150 kW, 175 kW, 200 kW, 250 kW, 300 kW, 350 kW, 400 kW, 450 kW, 500 kW, 600 kW, 700 kW, 800 kW, 900 kW or even 1000 kW.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam may be used according to at least one embodiment described herein. Advantages provided with the scanning beam include the larger scan width and the reduced possibility of local heating and failure of the windows.

Electron Guns—Windows

The extraction system for an electron accelerator that can be utilized for treating a feedstock (e.g., a lignocellulosic or cellulosic material) can include two window foils. The cooling gas in the two foil window extraction system can be a purge gas or a mixture, for example air, or a pure gas. In one embodiment the gas is an inert gas such as nitrogen, argon, helium and/or carbon dioxide. It is preferred to use a gas rather than a liquid since energy losses to the electron beam are minimized. Mixtures of pure gas can also be used, either pre-mixed or mixed in line prior to impinging on the windows or in the space between the windows. The cooling gas can be cooled, for example, by using a heat exchange system (e.g., a chiller) and/or by using boil off from a condensed gas (e.g., liquid nitrogen, liquid helium). Window foils are described in PCT/US2013/64332 filed Oct. 10, 2013, the full disclosure of which is incorporated herein by reference.

Heating and Throughput During Radiation Treatment

Several processes can occur in biomass when electrons from an electron beam interact with matter in inelastic collisions. For example, ionization of the material, chain scission of polymers in the material, cross linking of polymers in the material, oxidation of the material, generation of X-rays ("Bremsstrahlung") and vibrational excitation of molecules (e.g., phonon generation). Without being bound to a particular mechanism, the reduction in recalcitrance can be due to several of these inelastic collision effects, for example ionization, chain scission of polymers, oxidation and phonon generation. Some of the effects (e.g., especially X-ray generation), necessitate shielding and engineering barriers, for example, enclosing the irradiation processes in a concrete (or other radiation opaque material) vault. Another effect of irradiation, vibrational excitation, is equivalent to heating up the sample. Heating the sample by irradiation can help in recalcitrance reduction, but excessive heating can destroy the material, as will be explained below.

The adiabatic temperature rise ($\Delta T$) from adsorption of ionizing radiation is given by the equation: $\Delta T=D/Cp$: where D is the average dose in kGy, Cp is the heat capacity in J/g °C., and $\Delta T$ is the change in temperature in °C. A typical dry biomass material will have a heat capacity close to 2. Wet biomass will have a higher heat capacity dependent on the amount of water since the heat capacity of water is very high (4.19 J/g °C.). Metals have much lower heat capacities, for example, 304 stainless steel, has a heat capacity of 0.5 J/g °C. The calculated temperature change due to the instant adsorption of radiation in a biomass and stainless steel for various doses of radiation is shown in Table 6. In some cases, as indicated in the table, the temperatures are so high that the material decomposes (e.g., is volatilized, carbonized, and/or charred).

TABLE 6

Calculated Temperature increase for biomass and stainless steel.

| Dose (Mrad) | Estimated Biomass $\Delta T$ (° C.) | Steel $\Delta T$ (° C.) |
|---|---|---|
| 10 | 50 | 200 |
| 50 | 250 (decomposed) | 1000 |
| 100 | 500 (decomposed) | 2000 |
| 150 | 750 (decomposed) | 3000 |
| 200 | 1000 (decomposed) | 4000 |

High temperatures can destroy and/or modify the biopolymers in biomass so that the polymers (e.g., cellulose) are unsuitable for further processing. A biomass subjected to high temperatures can become dark, sticky and can give off odors, indicating decomposition. The stickiness can even make the material hard to convey. The odors can be unpleasant and be a safety issue. In fact, keeping the biomass below about 200° C. has been found to be beneficial in the processes described herein (e.g., below about 190° C., below about 180° C., below about 170° C., below about 160° C., below about 150° C., below about 140° C., below about 130° C., below about 120° C., below about 110° C., between about 60° C. and 180° C., between about 60° C. and 160° C., between about 60° C. and 150° C., between about 60° C. and 140° C., between about 60° C. and 130° C., between about 60° C. and 120° C., between about 80° C. and 180° C., between about 100° C. and 180° C., between about 120° C. and 180° C., between about 140° C. and 180° C., between about 160° C. and 180° C., between about 100° C. and 140° C., between about 80° C. and 120° C.).

It has been found that irradiation above about 10 Mrad is desirable for the processes described herein (e.g., reduction of recalcitrance). A high throughput is also desirable so that the irradiation does not become a bottleneck in processing the biomass. The treatment is governed by a Dose rate equation: $M=FP/D\cdot time$, where M is the mass of irradiated material (kg), F is the fraction of power that is adsorbed (unit less), P is the emitted power (kW=Voltage in MeV×Current in mA), time is the treatment time (sec) and D is the adsorbed dose (kGy). In an exemplary process where the fraction of adsorbed power is fixed, the Power emitted is constant and a set dosage is desired, the throughput (e.g., M, the biomass processed) can be increased by increasing the irradiation time. However, increasing the irradiation time without allowing the material to cool, can excessively heat the material as exemplified by the calculations shown above. Since biomass has a low thermal conductivity (less than about 0.1 $Wm^{-1}K^{-1}$), heat dissipation is slow, unlike, for example metals (greater than about 10 $Wm^{-1}K^{-1}$) which can dissipate energy quickly as long as there is a heat sink to transfer the energy.

Electron Guns—Beam Stops

In some embodiments the systems and methods (e.g., that utilize electron beam irradiation to irradiate a lignocellulosic or cellulosic feedstock) include a beam stop (e.g., a shutter). For example, the beam stop can be used to quickly stop or reduce the irradiation of material without powering down the electron beam device. Alternatively, the beam stop can be used while powering up the electron beam, e.g., the beam stop can stop the electron beam until a beam current of a desired level is achieved. The beam stop can be placed between the primary foil window and a secondary foil window. For example the beam stop can be mounted so that it is movable, that is, so that it can be moved into and out of the beam path. Even partial coverage of the beam can be used, for example, to control the dose of irradiation. The beam stop can be mounted to the floor, to a conveyor for the biomass, to a wall, to the radiation device (e.g., at the scan horn), or to any structural support. Preferably the beam stop is fixed in relation to the scan horn so that the beam can be effectively controlled by the beam stop. The beam stop can incorporate a hinge, a rail, wheels, slots, or other means allowing for its operation in moving into and out of the beam. The beam stop can be made of any material that will stop at least 5% of the electrons, e.g., at least 10%, 20%, 30%, 40%, 50%, 60%, 70%, at least 80%, 85%, 90%, 91%, 92%, 93%, 94%, 95%, 96%, 97%, 98%, 99%, or even about 100% of the electrons.

The beam stop can be made of a metal including, but not limited to, stainless steel, lead, iron, molybdenum, silver, gold, titanium, aluminum, tin, or alloys of these, or laminates (layered materials) made with such metals (e.g., metal-coated ceramic, metal-coated polymer, metal-coated composite, multilayered metal materials).

The beam stop can be cooled, for example, with a cooling fluid such as an aqueous solution or a gas. The beam stop can be partially or completely hollow, for example with cavities. Interior spaces of the beam stop can be used for cooling fluids and gases. The beam stop can be of any shape, including flat, curved, round, oval, square, rectangular, beveled, and wedged shapes.

The beam stop can have perforations so as to allow some electrons through, thus controlling (e.g., reducing) the levels of radiation across the whole area of the window, or in specific regions of the window. The beam stop can be a mesh formed, for example, from fibers or wires. Multiple beam stops can be used, together or independently, to control the irradiation. The beam stop can be remotely controlled, e.g., by radio signal or hard wired to a motor for moving the beam into or out of position.

Beam Dumps

The embodiments disclosed herein (e.g., the utilize ionizing radiation to irradiate a lignocellulosic or cellulosic feedstock) can also include a beam dump when utilizing a radiation treatment. A beam dump's purpose is to safely absorb a beam of charged particles. Like a beam stop, a beam dump can be used to block the beam of charged particles. However, a beam dump is much more robust than a beam stop, and is intended to block the full power of the electron beam for an extended period of time. They are often used to block the beam as the accelerator is powering up.

Beam dumps are also designed to accommodate the heat generated by such beams, and are usually made from materials such as copper, aluminum, carbon, beryllium, tungsten, or mercury. Beam dumps can be cooled, for example, using a cooling fluid that can be in thermal contact with the beam dump.

Biomass Materials

Lignocellulosic materials (e.g., feedstocks that are saccharified) include, but are not limited to, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), algae, seaweed, manure, sewage, and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases, even the root system of the plant.

Advantageously, no additional nutrients (other than a nitrogen source, e.g., urea or ammonia) are required during fermentation of corncobs or cellulosic or lignocellulosic materials containing significant amounts of corncobs.

Corncobs, before and after comminution, are also easier to convey and disperse, and have a lesser tendency to form explosive mixtures in air than other cellulosic or lignocellulosic materials, such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, and mixtures of any of these. For example paper products as described in U.S. application Ser. No. 13/396,365 ("Magazine Feedstocks" by Medoff et al., filed Feb. 14, 2012), the full disclosure of which is incorporated herein by reference.

Cellulosic materials can also include lignocellulosic materials which have been partially or fully de-lignified.

In some instances other biomass materials can be utilized, for example starchy materials. Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. Mixtures of starchy, cellulosic and/or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials that can be used as feedstock can include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femtoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems.

In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012, the full disclosure of which is incorporated herein by reference.

Any of the methods described herein can be practiced with mixtures of any biomass materials described herein.

Other Materials

Other materials (e.g., natural or synthetic materials), for example polymers, can be treated and/or made utilizing the methods, equipment and systems described herein. For example polyethylene (e.g., linear low density ethylene and high density polyethylene), polystyrenes, sulfonated polystyrenes, poly (vinyl chloride), polyesters (e.g., nylons, DACRON™, KODEL™), polyalkylene esters, poly vinyl esters, polyamides (e.g., KEVLAR™), polyethylene terephthalate, cellulose acetate, acetal, poly acrylonitrile, polycarbonates (e.g., LEXAN™), acrylics [e.g., poly (methyl methacrylate), poly(methyl methacrylate), polyacrylonitrile], polyurethanes, polypropylene, polybutadiene, polyisobutylene, polyacrylonitrile, polychloroprene (e.g. neoprene), poly(cis-1,4-isoprene) [e.g., natural rubber], poly (trans-1,4-isoprene) [e.g., gutta percha], phenol formaldehyde, melamine formaldehyde, epoxides, polyesters, poly amines, polycarboxylic acids, polylactic acids, polyvinyl alcohols, polyanhydrides, polyfluoro carbons (e.g., TEFLON™), silicons (e.g., silicone rubber), polysilanes, poly ethers (e.g., polyethylene oxide, polypropylene oxide), waxes, oils and mixtures of these. Also included are plastics, rubbers, elastomers, fibers, waxes, gels, oils, adhesives, thermoplastics, thermosets, biodegradable polymers, resins made with these polymers, other polymers, other materials and combinations thereof. The polymers can be made by any useful method including cationic polymerization, anionic polymerization, radical polymerization, metathesis polymerization, ring opening polymerization, graft polymerization, addition polymerization. In some cases the treatments disclosed herein can be used, for example, for radically initiated graft polymerization and cross linking. Composites of polymers, for example with glass, metals, biomass (e.g., fibers, particles), ceramics can also be treated and/or made.

Other materials that can be treated by using the methods, systems and equipment disclosed herein are ceramic materials, minerals, metals, inorganic compounds. For example, silicon and germanium crystals, silicon nitrides, metal oxides, semiconductors, insulators, cements, and/or conductors.

In addition, manufactured multipart or shaped materials (e.g., molded, extruded, welded, riveted, layered or combined in any way) can be treated, for example cables, pipes, boards, enclosures, integrated semiconductor chips, circuit boards, wires, tires, windows, laminated materials, gears, belts, machines, combinations of these. For example, treating a material by the methods described herein can modify the surfaces, for example, making them susceptible to further functionalization, combinations (e.g., welding) and/or treatment can cross link the materials.

For example, such materials can be mixed in with a lignocellulosic or cellulosic material and/or be included with the biomass feedstock.

Biomass Material Preparation—Mechanical Treatments

The biomass can be in a dry form, for example with less than about 35% moisture content (e.g., less than about 20%, less than about 15%, less than about 10%, less than about 5%, less than about 4%, less than about 3%, less than about 2%, or even less than about 1%). The biomass can also be delivered in a wet state, for example as a wet solid, a slurry or a suspension with at least about 10 wt % solids (e.g., at least about 20 wt %, at least about 30 wt %, at least about 40 wt %, at least about 50 wt %, at least about 60 wt %, at least about 70 wt %).

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-treatment processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration the desired biomass falls through the perforations or screen and thus biomasses larger than the perforations or screen are not irradiated. These larger materials can be re-processed, for example by comminuting, or they can simply be removed from processing. In another configuration, material that is larger than the perforations is irradiated and the smaller material is removed by the screening process or recycled. In this kind of a configuration, the conveyor itself (for example a part of the conveyor) can be perforated or made with a mesh. For example, in one particular embodiment, the biomass material may be wet and the perforations or mesh allow water to drain away from the biomass before irradiation.

Screening of material can also be by a manual method, for example by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-treatment processing can include heating the material. For example a portion of a conveyor conveying the biomass or other material can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, $CO_2$, Argon) over and/or through the biomass as it is being conveyed.

Optionally, pre-treatment processing can include cooling the material. Cooling material is described in U.S. Pat. No. 7,900,857 to Medoff, the entire disclosure of which in incorporated herein by reference. For example, cooling can be by supplying a cooling fluid, for example water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-treatment processing method can include adding a material to the biomass or other feedstocks. The additional material can be added by, for example, by showering, sprinkling and/or pouring the material onto the biomass as it is conveyed. Materials that can be added include, for example, metals, ceramics and/or ions as described in U.S. Pat. App. Pub. 2010/0105119 A1 (filed Oct. 26, 2009) and U.S. Pat. App. Pub. 2010/0159569 A1 (filed Dec. 16, 2009), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be delivered to a conveyor (e.g., vibratory conveyors used in the vaults herein described) by a belt conveyor, a pneumatic conveyor, a screw conveyor, a hopper, a pipe, manually or by a combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils of an electron gun (if such a device is used for treating the material).

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches).

Generally, it is preferred to convey the material as quickly as possible through the electron beam to maximize throughput. For example, the material can be conveyed at rates of at least 1 ft/min, e.g., at least 2 ft/min, at least 3 ft/min, at least 4 ft/min, at least 5 ft/min, at least 10 ft/min, at least 15 ft/min, 20, 25, 30, 35, 40, 45, 50 ft/min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through the radiation zone, optional post-treatment processing can be done. The optional post-treatment processing can, for example, be a process described with respect to the pre-irradiation processing. For example, the biomass can be screened, heated, cooled, and/or combined with additives. Uniquely to post-irradiation, quenching of the radicals can occur, for example, by quenching of radicals via the addition of fluids or gases (e.g., oxygen, nitrous oxide, ammonia, liquids), using pressure, heat, and/or the addition of radical scavengers. For example, the biomass can be conveyed out of the enclosed conveyor and exposed to a gas (e.g., oxygen) where it is quenched, forming carboxylated groups. In one embodiment the biomass is exposed during irradiation to the reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the carbohydrate-containing material. These processes can be applied before, during and/or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the carbohydrate-containing material, increase the surface area of the carbohydrate-containing material, and/or decrease one or more dimensions of the carbohydrate-containing material.

Alternatively, or in addition, the feedstock material can be treated with another treatment, for example chemical treatments, such as with an acid (HCl, $H_2SO_4$, $H_3PO_4$), a base (e.g., KOH and NaOH), a chemical oxidant (e.g., peroxides, chlorates, ozone), irradiation, steam explosion, pyrolysis, sonication, oxidation, chemical treatment. The treatments can be in any order and in any sequence and combinations. For example, the feedstock material can first be physically treated by one or more treatment methods, e.g., chemical treatment including and in combination with acid hydrolysis (e.g., utilizing HCl, $H_2SO_4$, $H_3PO_4$), radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. As another example, a feedstock material can be conveyed through ionizing radiation using a conveyor as described herein and then mechanically treated. Chemical treatment can remove some or all of the lignin (for example chemical pulping) and can partially or completely hydrolyze the material. The methods also can be used with pre-hydrolyzed material. The methods also can be used with material that has not been pre-hydrolyzed. The methods can be used with mixtures of hydrolyzed and non-hydrolyzed materials, for example with about 50% or more non-hydrolyzed material, with about 60% or more non-hydrolyzed material, with about 70% or more non-hydrolyzed material, with about 80% or more non-hydrolyzed material, or even with 90% or more non-hydrolyzed material.

In addition to size reduction, which can be performed initially and/or later in processing, mechanical treatment can also be advantageous for "opening up," "stressing," breaking, or shattering the carbohydrate-containing materials, making the cellulose of the materials more susceptible to chain scission and/or disruption of crystalline structure during the physical treatment.

Methods of mechanically treating the carbohydrate-containing material include, for example, milling or grinding. Milling may be performed using, for example, a hammer mill, ball mill, colloid mill, conical or cone mill, disk mill, edge mill, Wiley mill, grist mill or other mill. Grinding may be performed using, for example, a cutting/impact type grinder. Some non-limiting examples of grinders include stone grinders, pin grinders, coffee grinders, and burr grinders. Grinding or milling may be provided, for example, by a reciprocating pin or other element, as is the case in a pin mill. Other mechanical treatment methods include mechanical ripping or tearing, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 (filed Oct. 26, 2007), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material may be passed through a first screen, e.g., having an average opening size of 1.59 mm or less (1/16 inch, 0.0625 inch). If desired, the fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source.

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated carbohydrate-containing materials, are described in further detail in U.S. Pat. App. Pub. 2012/0100577, filed Oct. 18, 2011, the full disclosure of which is hereby incorporated herein by reference.

Sonication, Pyrolysis, Oxidation, Steam Explosion

If desired, one or more sonication, pyrolysis, oxidative, or steam explosion processes can be used instead of or in addition to irradiation and/or heating to reduce or further reduce the recalcitrance of the carbohydrate-containing material. Steam heating can optionally be utilized with the addition of an acid or base. For example, these processes can be applied before, during, and/or after irradiation. These processes are described in detail in U.S. Pat. No. 7,932,065 to Medoff, the full disclosure of which is incorporated herein by reference.

Intermediates and Products

Using the processes described herein, the biomass material can be converted to one or more products, such as energy, fuels, foods and materials. For example, intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, Kraft paper, corrugated paper or mixtures of these.

Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols (e.g., erythritol, glycol, glycerol, sorbitol threitol, arabitol, ribitol, mannitol, dulcitol, fucitol, iditol, isomalt, maltitol, lactitol, xylitol and other polyols), and methyl or ethyl esters of any of these alcohols. Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids, and their respective salts.

Any combination of the above products with each other, and/or of the above products with other products, which other products may be made by the processes described herein or otherwise, may be packaged together and sold as products. The products may be combined, e.g., mixed, blended, or co-dissolved, or may simply be packaged or sold together.

Any of the products or combinations of products described herein may be sanitized or sterilized prior to selling the products, e.g., after purification or isolation or even after packaging, to neutralize one or more potentially undesirable contaminants that could be present in the product(s). Such sanitation can be done with electron bombardment, for example, by a dosage of less than about 20 Mrad, e.g., from about 0.1 to 15 Mrad, from about 0.5 to 7 Mrad, or from about 1 to 3 Mrad.

The processes described herein can produce various by-product streams useful for generating steam and electricity to be used in other parts of the plant (co-generation) or sold on the open market. For example, steam generated from burning by-product streams can be used in a distillation process. As another example, electricity generated from burning by-product streams can be used to power electron beam generators used in pretreatment.

The by-products used to generate steam and electricity are derived from a number of sources throughout the process. For example, anaerobic digestion of wastewater can produce a biogas high in methane and a small amount of waste biomass (sludge). As another example, post-saccharification and/or post-distillate solids (e.g., unconverted lignin, cellulose, and hemicellulose remaining from the pretreatment and primary processes) can be used, e.g., burned, as a fuel.

Other intermediates and products, including food and pharmaceutical products, are described in U.S. Pat. App. Pub. 2010/0124583, published May 20, 2010, to Medoff, the full disclosure of which is hereby incorporated by reference herein.

Lignin Derived Products

The spent biomass (e.g., spent lignocellulosic material) from lignocellulosic processing by the methods described herein are expected to have a high lignin content, and in addition to being useful for producing energy through combustion in a Co-Generation plant, may have uses as other valuable products. For example, the lignin can be used as captured as a plastic, or it can be synthetically upgraded to other plastics. In some instances, it can also be converted to lignosulfonates, which can be utilized as binders, dispersants, emulsifiers or sequestrants.

When used as a binder, the lignin or a lignosulfonate can, e.g., be utilized in coal briquettes, in ceramics, for binding carbon black, for binding fertilizers and herbicides, as a dust suppressant, in the making of plywood and particle board, for binding animal feeds, as a binder for fiberglass, as a binder in linoleum paste, and as a soil stabilizer.

When used as a dispersant, the lignin or lignosulfonates can be used, for example in, concrete mixes, clay and ceramics, dyes and pigments, leather tanning, and in gypsum board.

When used as an emulsifier, the lignin or lignosulfonates can be used, e.g., in asphalt, pigments and dyes, pesticides, and wax emulsions.

As a sequestrant, the lignin or lignosulfonates can be used, e.g., in micro-nutrient systems, cleaning compounds and water treatment systems, e.g., for boiler and cooling systems.

For energy production, lignin generally has a higher energy content than holocellulose (cellulose and hemicellulose) since it contains more carbon than homocellulose. For example, dry lignin can have an energy content of between about 11,000 and 12,500 BTU per pound, compared to 7,000 and 8,000 BTU per pound of holocellulose. As such, lignin can be densified and converted into briquettes and pellets for burning. For example, the lignin can be converted into pellets by any method described herein. For a slower burning pellet or briquette, the lignin can be crosslinked, for example, by applying a radiation dose of between about 0.5 Mrad and 5 Mrad. Crosslinking can make a slower burning form factor. The form factor, such as a pellet or briquette, can be converted to a "synthetic coal" or charcoal by pyrolyzing in the absence of air, e.g., at between 400 and 950° C. Prior to pyrolyzing, it can be desirable to crosslink the lignin to maintain structural integrity.

Saccharification

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Therefore, the treated biomass materials can be saccharified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/0100577 by Medoff et al., published on Apr. 26, 2012, the entire contents of which are incorporated herein.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the carbohydrate-containing material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published as WO 2010/135380, the full disclosure of which is incorporated herein by reference.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics may inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial or preservative properties may be used. Preferably the antimicrobial additive(s) are food-grade.

A relatively high concentration solution can be obtained by limiting the amount of water added to the carbohydrate-containing material with the enzyme. The concentration can be controlled, e.g., by controlling how much saccharification takes place. For example, the concentration can be increased by adding more carbohydrate-containing material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

Saccharifying Agents

Suitable enzymes, such as amylases and/or cellulolytic enzymes include cellulases from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incolora-*

*tum*, and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additional strains that can be used may include, but are not limited to, *Trichoderma* (particularly *T. viride*, *T. reesei*, and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

In addition to or in combination to enzymes, acids, bases and other chemicals (e.g., oxidants) can be utilized to saccharify lignocellulosic and cellulosic materials. These can be used in any combination or sequence (e.g., before, after and/or during addition of an enzyme). For example, strong mineral acids can be utilized (e.g. HCl, $H_2SO_4$, $H_3PO_4$) and strong bases (e.g., NaOH, KOH).

Sugars

In the processes described herein, for example after saccharification, sugars (e.g., glucose and xylose) can be isolated. For example sugars can be isolated by precipitation, crystallization, chromatography (e.g., simulated moving bed chromatography, high pressure chromatography), centrifugation, extraction, any other isolation method known in the art, and combinations thereof.

Hydrogenation and Other Chemical Transformations

The processes described herein can include hydrogenation. For example glucose and xylose can be hydrogenated to sorbitol and xylitol respectively. Hydrogenation can be accomplished by use of a catalyst (e.g., Pt/gamma-$Al_2O_3$, Ru/C, Raney Nickel, or other catalysts known in the art) in combination with $H_2$ under high pressure (e.g., 10 to 12000 psi, 100 to 10000 psi). Other types of chemical transformation of the products from the processes described herein can be used, for example production of organic sugar derived products such (e.g., furfural and furfural-derived products). Chemical transformations of sugar derived products are described in U.S. Ser. No. 13/934,704 filed Jul. 3, 2013, the entire disclosure of which is incorporated herein by reference in its entirety.

Fermentation

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$, or mixtures thereof. Additionally, the mixture may have a constant purge of an inert gas flowing through the tank during part of or all of the fermentation. In some cases, anaerobic conditions can be achieved or maintained by carbon dioxide production during the fermentation, and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance. Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub. 2012/0052536, filed Jul. 15, 2011, the complete disclosure of which is incorporated herein by reference.

"Fermentation" includes the methods and products that are disclosed in applications No. PCT/US2012/71093 published Jun. 27, 2013, PCT/US2012/71907 published Jun. 27, 2012, and PCT/US2012/71083 published Jun. 27, 2012 the contents of which are incorporated by reference herein in their entirety.

Mobile fermenters can be utilized, as described in International App. No. PCT/US2007/074028 (which was filed Jul. 20, 2007, and published as WO 2008/011598) and has a US issued U.S. Pat. No. 8,318,453, the contents of which are incorporated by reference herein in its entirety. Similarly, the saccharification equipment can be mobile. Further, saccharification and/or fermentation may be performed in part or entirely during transit.

Fermentation Agents

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protist (including, but not limited to, e.g., a slime mold), or an alga. When the organisms are compatible, mixtures of organisms can be utilized.

Suitable microorganisms used for fermentation have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus*, *S. uvarum*), the genus *Kluyveromyces*, (including, but not limited to, *K. marxianus*, *K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. tyrobutyricum C. saccharobutylicum, C. Puniceum, C. beijernckii*, and *C. acetobutylicum*), *Moniliella* spp. (including but not limited to *M. pollinis, M. tomentosa, M. madida, M. nigrescens, M. oedocephali, M. megachiliensis*), *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus Torula (e.g., *T. corallina*).

Many such microbial strains are publicly available, either commercially or through depositories such as the ATCC (American Type Culture Collection, Manassas, Va., USA), the NRRL (Agricultural Research Service Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, RED STAR®/Lesaffre Ethanol Red (available from Red Star/Lesaffre, USA), FALK) (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Distillation

After fermentation, the resulting fluids can be distilled using, for example, a "beer column" to separate ethanol and other alcohols from the majority of water and residual solids. The distillation can be done under vacuum (e.g., to reduce decomposition of products in the solution such as sugars). The vapor exiting the beer column can be at least 35% by weight (e.g., at least 40%, at least 50% b or at least 90% by weight) ethanol and can be fed to a rectification column. A mixture of nearly azeotropic (e.g., at least about 92.5% ethanol and water from the rectification column can be purified to pure (e.g., at least about 99.5% or even about 100%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to wastewater treatment to prevent build-up of low-boiling compounds.

Conveying Systems

Various conveying systems can be used to convey the biomass material, for example, to a vault and under an electron beam in a vault. Exemplary conveyors are belt conveyors, pneumatic conveyors, screw conveyors, carts, trains, trains or carts on rails, elevators, front loaders, backhoes, cranes, various scrapers and shovels, trucks, and throwing devices can be used. For example, vibratory conveyors can be used in various processes described herein. Vibratory conveyors are described in PCT/US2013/64289 filed Oct. 10, 2013 the full disclosure of which is incorporated herein by reference.

Optionally, one or more conveying systems can be enclosed. When using an enclosure, the enclosed conveyor can also be purged with an inert gas so as to maintain an atmosphere at a reduced oxygen level. Keeping oxygen levels low avoids the formation of ozone which in some instances is undesirable due to its reactive and toxic nature. For example, the oxygen can be less than about 20% (e.g., less than about 10%, less than about 1%, less than about 0.1%, less than about 0.01%, or even less than about 0.001% oxygen). Purging can be done with an inert gas including, but not limited to, nitrogen, argon, helium or carbon dioxide. This can be supplied, for example, from boil-off of a liquid source (e.g., liquid nitrogen or helium), generated or separated from air in situ, or supplied from tanks. The inert gas can be recirculated and any residual oxygen can be removed using a catalyst, such as a copper catalyst bed. Alternatively, combinations of purging, recirculating, and oxygen removal can be done to keep the oxygen levels low.

The enclosed conveyor can also be purged with a reactive gas that can react with the biomass. This can be done before, during or after the irradiation process. The reactive gas can be, but is not limited to, nitrous oxide, ammonia, oxygen, ozone, hydrocarbons, aromatic compounds, amides, peroxides, azides, halides, oxyhalides, phosphides, phosphines, arsines, sulfides, thiols, boranes and/or hydrides. The reactive gas can be activated in the enclosure, e.g., by irradiation (e.g., electron beam, UV irradiation, microwave irradiation, heating, IR radiation), so that it reacts with the biomass. The biomass itself can be activated, for example by irradiation. Preferably the biomass is activated by the electron beam, to produce radicals which then react with the activated or unactivated reactive gas, e.g., by radical coupling or quenching.

Purging gases supplied to an enclosed conveyor can also be cooled, for example, below about 25° C., below about 0° C., below about −40° C., below about −80° C., below about −120° C. For example, the gas can be boiled off from a compressed gas such as liquid nitrogen or sublimed from solid carbon dioxide. As an alternative example, the gas can be cooled by a chiller or part of or the entire conveyor can be cooled.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (e.g., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method comprising:
    irradiating a plurality of waste biomass material portions, each of the plurality of waste biomass material portions being irradiated to a different dose;
    forming free radicals in the plurality of waste biomass material portions;
    quenching at least a portion of the free radicals in each of the plurality of waste biomass material portions to form a plurality of quenched waste biomass material portions;
    measuring a response associated with a concentration of remaining free radicals in each of the plurality of quenched waste biomass material portions;
    producing a curve of the responses versus the doses; and
    determining an optimal amount of recalcitrance reduction of the plurality of waste biomass material portions to facilitate saccharification of the waste biomass material portions from the curve of the responses versus the doses.

2. The method of claim 1, wherein irradiating the plurality of waste biomass material portions includes irradiating the plurality of waste biomass material portions with an electron beam.

3. The method of claim 1, wherein a same procedure is utilized to quench the at least a portion of the free radicals in each of the plurality of waste biomass material portions.

4. The method of claim 3, wherein the procedure includes heating the plurality of waste biomass material portions at a predetermined temperature for a predetermined time.

5. The method of claim 4, wherein the predetermined temperature is at least 40 degrees Celsius.

6. The method of claim 4, wherein the predetermined time is at least thirty minutes.

7. The method of claim 4, wherein the plurality of waste biomass material portions are heated in air.

8. The method of claim 4, wherein the waste biomass material portions are heated in a liquid.

9. The method of claim 4, further comprising cooling the plurality of waste biomass material portions to room temperature or below subsequent to heating the plurality of waste biomass material portions and prior to measuring the response.

10. The method of claim 9, further comprising storing the plurality of waste biomass material portions at a temperature below −50 degrees Celsius prior to measuring the response.

11. The method of claim 3, wherein the procedure includes exposing the plurality of waste biomass material portions to oxygen.

12. The method of claim 1, wherein measuring the response includes measuring an electron spin response of each of the plurality of waste biomass material portions.

13. The method of claim 1, further comprising determining a saturation dose for the waste biomass material portions from the curve of the responses versus the doses.

14. The method of claim 1, further comprising determining an optimal dose to facilitate saccharification of the waste biomass material portions from the curve of the responses versus the doses.

15. The method of claim 14, further comprising:
    irradiating a sample of the waste biomass material to the optimal dose; and
    saccharifying the sample of the waste biomass material.

16. The method of claim 1, further comprising:
    irradiating a sample of the waste biomass material; and
    determining a dose of radiation the sample of waste biomass material received from the curve of the responses versus the doses.

17. The method of claim 1, wherein the method is performed on a plurality of portions of lignocellulosic waste biomass material.

18. A method comprising:
    forming free radicals in a sample of waste biomass materials by irradiating the sample of waste biomass materials to a dose;
    quenching at least a portion of the free radicals in sample of waste biomass materials;
    measuring a response associated with a concentration of remaining free radicals in the sample of waste biomass materials after quenching;
    repeating the acts of forming the free radicals, quenching the at least a portion of the free radicals, and measuring the response in the sample of waste biomass materials while recording a cumulative dose applied to the sample of waste biomass materials until a measured response is no higher than a response measured in a previous iteration of performing the acts of forming the free radicals, quenching the at least a portion of the free radicals, and measuring the response in the sample of waste biomass materials; and
    producing a curve of the responses versus the cumulative doses; and
    determining an optimal amount of recalcitrance reduction of the waste biomass materials to facilitate saccharification of the biomass from the curve of the responses versus the cumulative doses.

19. The method of claim 18, further comprising determining an optimal dose that will facilitate saccharification of the waste biomass material to obtain highest sugar yields at a lowest cost from the curve of the responses versus the cumulative doses.

20. The method of claim 18, wherein the method is performed on a sample of lignocellulosic waste biomass material.

* * * * *